US008138364B2

(12) United States Patent
Marks et al.

(10) Patent No.: US 8,138,364 B2
(45) Date of Patent: Mar. 20, 2012

(54) TRANSPARENT CONDUCTING OXIDE THIN FILMS AND RELATED DEVICES

(75) Inventors: Tobin J. Marks, Evanston, IL (US); Jun Ni, Quincy, MA (US); Anchuan Wang, San Jose, CA (US); Yu Yang, Santa Clara, CA (US); Andrew Metz, Beaverton, OR (US); Shu Jin, Shanghai (CN); Lian Wang, Lowell, MA (US)

(73) Assignee: Northwestern University, Evanston, IL (US)

( * ) Notice: Subject to any disclaimer, the term of this patent is extended or adjusted under 35 U.S.C. 154(b) by 618 days.

(21) Appl. No.: 11/726,624

(22) Filed: Mar. 22, 2007

(65) Prior Publication Data

US 2008/0024055 A1    Jan. 31, 2008

Related U.S. Application Data

(63) Continuation-in-part of application No. 10/228,521, filed on Aug. 27, 2002, now abandoned.

(60) Provisional application No. 60/784,658, filed on Mar. 22, 2006, provisional application No. 60/315,159, filed on Aug. 27, 2001.

(51) Int. Cl.
*C07F 3/06* (2006.01)
(52) U.S. Cl. ...................................... 556/130
(58) Field of Classification Search .............. 556/130
See application file for complete search history.

(56) References Cited

U.S. PATENT DOCUMENTS 6,030,454 A * 2/2000 Roeder et al. ................. 117/104

OTHER PUBLICATIONS

Ni et al. "MOCVD-Derived Highly Transparent, Conductive Zinc- and Tin-Doped Indium Oxide Thin Films: Precursor Synthesis, Metastable Phase Film Growth and Characterization, and Application as Anodes in Polymer Light-Emitting Diodes" Journal of the American Chemical Society, 2005, vol. 127, pp. 5613-5624.*
Fenton et al. "The reaction of 2,3,6,7-tetrahydro-(2-hydroxyphenyl)-7-phenyl-1-H-1,4-diazepine with copper(II) and nickel(II) salts" Transition Metal Chemistry, 1985, vol. 10, No. 11, pp. 437-438.*
Babcock et al. (CAS Accession No. 2001:183240).*
Malinsky, J.E.; Jabbour, G.E.; Shaheen, S.E.; Anderson, J.D.; Richter, A.G.; Marks, T.J.; Armstrong, N.R.; Kippelen, B.; Dutta, P.; Peyghambarian, N. Self-Assembly Processes for Organic LED Electrode Passivation and Charge Injection Balance. Adv. Mater. 1999, 11, No. 3.
Ishii, H.; Sugiyama, K.; Ito, E.; Seki, K. Energy Level Alignment and Interfacial Electronic Structures at Organic/Metal and Organic/Organic Interfaces. Adv. Mater. 1999, 11, No. 8.
Yan, H.; Huang, Q.; Cui, J.; Veinot, J.G.C.; Kern, M.M.; Marks, T.J. High-Brightness Blue Light-Emitting Polymer Diodes via Anode Modification Using a Self-Assembled Monolayer. Adv. Mater. May 16, 2003, 15, No. 10.

Kido, J.; Hongawa, K.; Okuyama, K.; Nagai, K. Bright Blue Electroluminescence from Poly(N-vinylcarbazole) Appl. Phys. Lett. 63 (19), Nov. 8, 1993, pp. 2627-2629.
Phillips, J.M.; Kwo, J.; Thomas, G.A.; Carter, S.A.; Cava, R.J.; Hou, S.Y.; Krajewski, J.J.; Marshall, J.H.; Peck, W.F.; Rapkine, D.H.; Van Dover, R.B. Transparent Conducting Thin Films of GaInO3. Appl. Phys. Lett. 65 (1), Jul. 4, 1994, pp. 115-117.
Park, Y.; Choong, V.; Gao, Y.; Hsieh, B.R.; Tang, C.W. Work Function of Indium Tin Oxide Transparent Conductor Measured by Photoelectron Spectroscopy. Appl. Phys. Lett. 68 (19), May 6, 1996, pp. 2699-2701.
Schlatmann, A.R.; Floet, D.W.; Hilberer, A.; Garten, F.; Smulders, P.J.M.; Klapwijk, T.M.; Hadziioannou, G. Indium Contamination from the Indium-Tin-Oxide Electrode in Polymer Light-Emitting Diodes. Appl. Phys. Lett. 69 (12), Sep. 16, 1996, pp. 1764-1766.
Yan, Y.; Pennycook, S.J.; Dai, J.; Chang, R.P.H.; Wang, A.; Marks, T.J. Polytypoid Structures in Annealed In2O3-ZnO Films. Appl. Phys. Lett. 73 (18), Nov. 2, 1998, pp. 2585-2587.
Wang, A.; Dai, J.; Cheng, J.; Chudzik, M.P.; Marks, T.J.; Chang, R.P.H.; Kannewurf, C.R. Charge Transport, Optical Transparency, Microstructure, and Processing Relationships in Transparent Conductive Indium-Zinc Oxide Films Grown by Low-Pressure Metal-Organic Chemical Vapor Deposition. Appl. Phys. Lett. 73 (3), Jul. 20, 1998, pp. 327-329.
Schlaf, R.; Parkinson, B.A.; Lee, P.A.; Nebesny, K.W.; Armstrong, N.R. Determination of Frontier Orbital Alignment and Band Bending at an Organic Semiconductor Heterointerface by Combined X-ray and Ultraviolet Photoemission Measurements. Appl. Phys. Lett. 73 (8), Aug. 24, 1998, 1026-1028.
Utsunomiya, K. Gas Chromatography of Aluminum, Gallium, and Indium β-Diketone Chelates. Bulletin of the Chem. Soc. of Japan, v. 44, 2688-2693 (1971).
Bos, K.D.; Budding, H.A.; Bulten, E.J.; Noltes, J.G. Tin(II) Bis(1,3-Diketonates) and Tin(II) 1,3-Diketonate Chlorides. Inorg. Nucl. Chem. Lett., v. 9, 961-963 (1973).
Zhang, C.; Braun, D.; Heeger, A.J. Light-Emitting Diodes from Partially Conjugated Poly(p-phenylene vinylene). J. Appl. Phys. 73 (10), May 15, 1993, pp. 5177-5180.
Scott, J.C.; Kaufman, J.H.; Brock, P.J.; Depietro, R.; Salem, J.; Goitia, J.A. Degradation and Failure of MEH-PPV Light-Emitting Diodes. J. Appl. Phys. 79 (5), Mar. 1, 1996, pp. 2745-2751.
Milliron, D.J.; Hill, I.G.; Shen, C.; Kahn, A.; Schwartz, J. Surface Oxidation Activates Indium Tin Oxide for Hole Injection. J. Appl. Phys. 87 (1), Jan. 1, 2000, pp. 572-576.
Ni, J.; Yan, H.; Wang, A.; Yang, Y.; Stern, C.L.; Metz, A.W.; Jin, S.; Wang, L.; Marks, T.J.; Ireland, J.R.; Kannewurf, C.R. MOCVD-Derived Highly Transparent, Conductive Zinc- and Tin-Doped Indium Oxide Thin Films: Precursor Synthesis, Metastable Phase Film Growth and Characterization, and Application as Anodes in Polymer Light-Emitting Diodes. J. Am. Chem. Soc. 127, 5613-5624, 2005.

(Continued)

*Primary Examiner* — Joseph Kosack
(74) *Attorney, Agent, or Firm* — Reinhart Boerner Van Deuren s.c.

(57) ABSTRACT

Transparent conducting oxide thin films having a reduced indium content and/or an increased tin content are provided. In addition, processes for producing the same, precursors for producing the same, and transparent electroconductive substrate for display panels and organic electroluminescence devices, both including the transparent conducting oxide thin films, are provided.

1 Claim, 16 Drawing Sheets

OTHER PUBLICATIONS

Ewings, P.F.R.; Harrison, P.G.; Fenton, D.E. Derivatives of Divalent Germanium, Tin, and Lead. Part V. Bis (pentane-2,4-dionato)-, Bis(1,1,1-trifluoropentane-2,4-dionato)-, and Bis(1,1,1,5,5,5-hexafluoropentane-2,4-dionato)-tin (II). J. Chem. Soc., Dalton Transactions, Inorg. Chem. (9), 821-826 (1975).

Lim, E.; Jung, B-J.; Shim, H-K. Synthesis and Characterization of a New Light-Emitting Fluorene—Thieno[3,2-b] thiophene-Based Conjugated Copolymer. Macromolecules, 36, 4288-4293, 2003.

Wang, A.; Cheng, S.C.; Belot, J.A.; McNeely, R.J.; Cheng, J.; Marcordes, B.; Marks, T.J.; Dai, J.Y.; Chang, R.P.H.; Schindler, J.L.; Chudzik, M.P.; Kannewurf, C.R. Metalorganic-Chemical-Vapor-Deposition Routes to Films of Transparent Conducting Oxides. Mat. Res. Soc. Symp., 1998, 495 3 Abstract.

Wang, A.; Edleman, N.L.; Babcock, J.R.; Marks, T.J.; Lane, M.A.; Brazis, P.W.; Kannewurf, C.R. Metal-Organic Chemical Vapor Deposition of Zn-In-Sn-O and Ga-In-Sn-O Transparent Conducting Oxide Thin Films. Mat. Res. Soc. Symp., 2000, 607, 345 Abstract.

Freeman, A.J.; Poeppelmeier, K.R.; Mason, T.O.; Chang, R.P.H.; Marks, T.J. Chemical and Thin-Film Strategies for New Transparent Conducting Oxides. MRS Bulletin, Aug. 2000, pp. 45-51.

Ginley, D.S.; Bright, C. Transparent Conducting Oxides. MRS Bulletin, Aug. 2000, pp. 15-18.

Li, W.; ,Malinsky, J.E.; Chou, H.; MA, W.; Geng, L.; Marks, T.J.; Jabbour, G.E.; Shaheen, S.E.; Kippelen, B.; Peyghambarian, N.; Dutta, P.; Richter, A.G.; Armstrong, N.R.; Lee, P.A.; Anderson, J.E. Molecular self-assembly routes to electroluminescent multilayer structures. Polymer Preprints (Am. Chem. Soc., Div. of Polymer Chemistry), 39(2), 1083-1084, 1998.

Jablonsky, Z.; Rychlowska-Himmel, I. Indium Chelates with 1,3-diketones and their Monothioderivatives—I. Preparation, Analysis and I.R. Spectra. Spectrochimica Acta, (35A), 1297-1301, 1979.

Chkoda, L.; Heske, C.; Sokolowski, M.; Umbach, E.; Steuber, F.; Staudigel, J.; Stobel, M.; Simmerer, J. Work Function of ITO Substrates and Band-Offsets at the TPD/ITO Interface Determined by Photoelectron Spectroscopy. Synthetic Metals, 111-112, 315-319, 2000.

\* cited by examiner

A.

B.

I (TAA)                II (crosslinked form)

Alq (ETL/EML)          TPD (HTL)

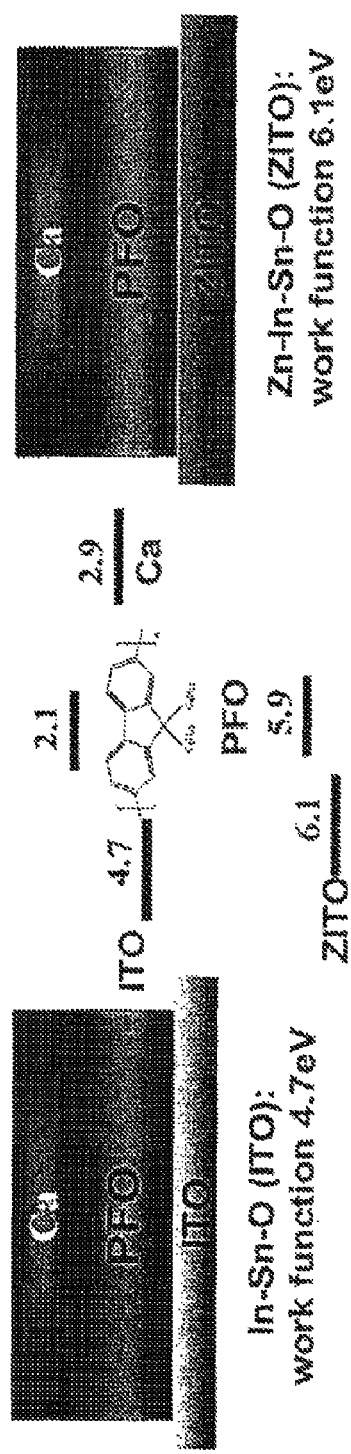
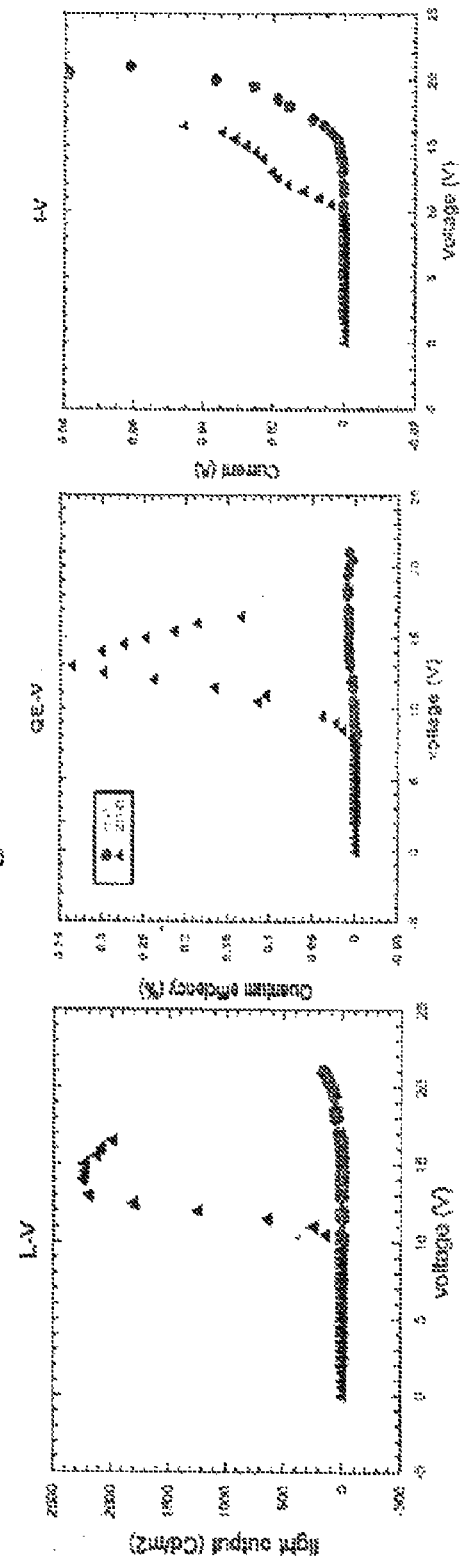
Figure 4
Figure 5A
Figure 5B
Figure 5C (A)

(B)

(C)

(A)

(B)

(A)

(B)

(A)

(B)

(C)

(A)

(B)

Poly(9,9-dioctylfluorene) (PFO)

Polystyrenesulfonate-poly(3,4-ethylenedioxythiophene)

(PEDOT–PSS)

TRANSPARENT CONDUCTING OXIDE THIN FILMS AND RELATED DEVICES

This application claims priority benefit of provisional application Ser. No. 60/784,658, filed on Mar. 22, 2006, the entirety of which is incorporated herein by reference, and claims priority from and is a continuation in part of application Ser. No. 10/228,521, filed on Aug. 27, 2002 now abandoned, which claims priority benefit of provisional application Ser. No. 60/315,159, filed Aug. 27, 2001, each of which is incorporated herein by reference in its entirety.

The United States government has certain rights to this invention pursuant to Grant Nos. CHE-0201767 and DMR-0076097 from the United States National Science Foundation and Grant No. N00014-95-1-1-1319 from the Office of Naval Research, all to Northwestern University.

BACKGROUND

Transparent conducting oxide (TCO) thin films have wide applications in optoelectronics. For example, they have been widely used as transparent electrodes in various devices including flat panel displays such as liquid crystal displays (LCDs) and plasma panel displays (PDPs), light emitting diodes (LEDs), solar cells, and thin film transistors. Transparent conductive thin films also have applications as window coatings that confer heat-reflecting, antistatic, and/or defogging properties.

Various TCO materials have been identified and studied in bulk forms and in thin films. They include tin oxide ($SnO_2$) doped with antimony or fluorine, zinc oxide (ZnO) doped with aluminum or gallium, and indium oxide ($In_2O_3$) doped with tin. Tin-doped indium oxide (ITO) is the current TCO of choice in most industrial applications, having conductivity of about 2000-4000 S/cm for polycrystalline thin films, a work function of about 4.5 eV, and optical absorption in the blue-green spectral region.

Furthermore, due to recent high demands for flat panel displays, there has been a growing supply deficit for indium. As a result, the price of indium has increased drastically. It was reported that the average price for indium in 2005 was US $900 per kilogram. This presents significant challenges to large-scale introduction of next-generation flat panel display and photovoltaic technologies, as commercial ITO thin films often have indium content near 90 cation %.

Impressive scientific and technological progress has recently been achieved in the area of organic light-emitting diodes (OLEDs), driven by potential applications in a large variety of display technologies. An equal fundamental research motivation has been the desire to better understand and control charge injection into, charge migration through, and radiative recombination in, molecular and macromolecular solids. Over the past few years, increasing activity has focused on improving charge injection efficiency at both OLED cathode/organic and anode/organic interfaces. (See, e.g., J. E. Malinsky, G. E. Jabbour, S. E. Shaheen, J. D. Anderson, A. G. Richter, N. R. Armstrong, B. Kippelen, P. Dutta, N. Peyghambarian, T. J. Marks, *Adv. Mater.* 1999, 11, 227). Low work function metals (e.g., Ca, Mg) and combinations with other atmospherically stable metals (e.g., Ag, Al) have been implemented as cathodes, to afford improved luminous quantum efficiencies and lower operating voltages. (C. Zhang, D. Braun, A. J. Heeger, *J. Appl. Phys.* 1993, 73, 5177; J. Kido, K. Hongawa, K. Okuyama, K. Nagai, *Appl. Phys. Lett.* 1993, 63, 2627.) In contrast, relatively few materials have been explored as alternatives to Sn-doped $In_2O_3$ (ITO) as OLED anodes. As an n-doped, degenerate wide band gap semiconductor, ITO is used in numerous opto-electronics applications (e.g., photovoltaic cells, flat panel liquid crystal displays, "smart" windows, etc.) because of good transmittance in the visible and near-IR, low electrical resistivity, and easy processibility. (H. L. Hartnagel, A. L. Dawar, A. K. Jain, C. Jagadish, *Semiconducting Transparent Thin Films*, Institute of Physics, Bristol. 1995; Special Issue on Transparent Conducting Oxides, (Eds: D. S. Ginley, C. Bright), *MRS Bulletin*. August 2000, Vol. 25.)

However, the chemical and electronic properties of ITO are far from optimum for current and future generation OLEDs. Drawbacks include (1) deleterious diffusion of oxygen and In into proximate organic charge transporting/emissive layers (A. R. Schlatmann, D. W. Floet, A. Hillberer, F. Garten, P. J. M. Smulders, T. M. Klapwijk, G. Hadziioannou, *Appl. Phys. Lett.* 1996, 69, 1764; J. C. Scott, J. H. Kaufman, P. J. Brock, R. Dipietro, J. Salem, J. A. Goitia, *J. Appl. Phys.* 1996, 79, 2745), (2) imperfect (injection barrier-creating) work function alignment with respect to typical hole transport layer (HTL) HOMO levels (L. Chkoda, C. Heske, M. Sokolowski, E. Umbach, F. Steuber, J. Staudigel, M. Stossel, J. Simmerer, *Synthetic Metals* 2000, 111, 315; Y. Park, V. Choong, Y. Gao, B. R. Hsieh, C. W. Tang, *Appl. Phys. Lett.* 1996, 68, 2699; D. J. Milliron, I. G. Hill, C. Shen, A. Kahn, J. Schwartz, *J. Appl. Phys.* 2000, 87, 572), and (3) poor transparency in the blue region. (J. M. Philips, J. Kwo, G. A. Thomas, S. A. Carter, R. J. Cava, S. Y. Hou, J. J. Krajewski, J. H. Marshall, W. F. Peck, D. H. Rapkine, R. B. V. Dover, *Appl. Phys. Lett.* 1994, 65, 115.) Several alternative materials have been recently examined as anodes, including TiN, doped Si, Al-doped Zn, and F-doped $SnO_2$. However, all such materials suffer from some combination of poor optical transparency and/or significantly lower work functions than ITO, resulting in poor Fermi level energetic alignment with HTL HOMOs. Efforts continue in the art for an effective alternative to ITO and use thereof in OLED anode and device structures.

Accordingly, there is a desire in the art for low indium content alternative TCO materials that have opto-electrical properties that are superior or comparable to ITO. Preparation techniques that can be used to improve the opto-electrical properties of both existing and new TCO materials also are desired.

Meanwhile, metal-organic chemical vapor deposition (MOCVD) recently has been identified as an attractive growth process for ZITO (zinc-indium-tin-oxide) thin films. To achieve effective growth of thin films by MOCVD, a suitable metal-organic precursor is critical. Ideally, the metal-organic precursor is both highly volatile and thermally stable, and can be easily handled. Most current MOCVD precursors lack at least one of these characteristics.

For example, while zinc is an important component in many new TCO materials, current zinc precursors for MOCVD processes suffer from either poor reproducibility in growth processes or chemical instability. Several zinc compounds, such as liquid diethyl zinc and dimethyl zinc, zinc acetate, and $Zn(hfa)_2 \cdot 2H_2O$.polyether adducts (hfa=1,1,1,5,5,5-hexafluoro-2,4-pentanedionato), have been demonstrated as MOCVD precursors in the growth of zinc-containing oxide thin films. However, diethyl zinc and dimethyl zinc are volatile, pyrophoric liquids which must be handled in an inert atmosphere. They are highly reactive materials and difficult to control in the deposition of multi-component films. In the case of zinc acetate and $Zn(hfa)_2 \cdot 2H_2O$.polyether, the water of hydration must be removed before these precursors can be used effectively. The volatility of zinc acetate also decreases markedly over prolonged deposition runs. $Zn(dpm)_2$ (dpm=2,2,6,6-tetramethyl-3,5-heptanedionato) is another widely-used MOCVD precursor which does not require a co-reactant or pre-treatment. However, it is a solid over a broad temperature range and suffers from sintering at elevated temperatures and during film growth runs. Sintering decreases the surface area of the solid precursor and thereby causes the flux of gaseous zinc species being transported to vary during the film growth process, seriously compromising film compositional control.

Accordingly, there is a desire in the art for improved MOCVD precursors that can be used to prepare TCO thin films.

SUMMARY OF THE INVENTION

In light of the foregoing, the present teachings provide transparent, conducting oxide thin films that offer opto-electrical properties superior or comparable to current ITO materials but having a reduced indium content. The present teachings also provide methods of preparing these transparent, conducting oxide thin films. The present teachings provide precursors that can be used to prepare these transparent, conducting oxide thin films. The present teachings further provide transparent conductive composites that can comprise such transparent, conducting oxide thin films. These transparent conductive substrates may be used in flat panel displays and/or electroluminescent devices.

In one non-limiting aspect, the invention can provide a zinc-indium-tin-oxide (ZITO) thin film that can have a relative tin (Sn) cation content [rcc(Sn)] greater than or equal to about 10% and a conductivity (S) greater than or equal to about 2300 S/cm at 25° C. In some embodiments, the ZITO thin film can have a relative Sn cation content greater than about 10%, greater than about 20%, greater than about 30%, or greater than about 33%. In certain embodiments, the ZITO thin film can have a relative indium (In) cation content [rcc (In)] less than about 70%, less than about 60%, less than about 50%, less than about 45%, or less than or equal to about 44%. In some embodiments, the atomic ratio of tin to indium (Sn/In) can be between about 0.40 and about 1.00, more specifically, between about 0.40 and about 0.75, or between about 0.75 and about 1.00. In certain embodiments, the conductivity can be greater than about 1400 S/cm at 25° C., greater than about 1700 S/cm at 25° C., greater than about 2000 S/cm at 25° C., greater than about 2500 S/cm at 25° C., greater than about 2700 S/cm at 25° C., greater than about 2800 S/cm at 25° C., or greater than or equal to about 2900 S/cm at 25° C. In some embodiments, the ZITO thin film can have a Q value greater than or equal to about 5300, wherein Q=S/rcc(In).

More specifically, in some embodiments, the ZITO thin film can include $SnO_2/ZnO$-cosubstituted $In_2O_3$. The thin film can be a phase-pure solid solution with a polycrystalline structure. The thin film can have a thickness between about 200 nm and about 2000 nm. Particularly, the film thickness can be less than or equal to about 1000 nm. In some embodiments, the thin film can have a surface root mean square (rms) roughness less than or equal to about 5 nm.

In some embodiments, the average transmittance ($T_{avg}$) of the thin film can be greater than or equal to about 80% between about 400 nm and about 1500 nm. For example, the thin film can have a light absorption coefficient (A) less than about 2700 $cm^{-1}$ at about 550 nm.

Another aspect of the invention can provide a zinc-indium-tin-oxide (ZITO) thin film that can have a relative indium cation content [rcc(In)] less than or equal to about 45% and a conductivity (S) greater than or equal to about 2300 S/cm at 25° C. In certain embodiments, the ZITO thin film can have a relative In cation content less than or equal to about 40%. Such ZITO thin films can have one or more of the properties or characteristics described above.

In a further aspect, the invention can provide a composite comprising any of the transparent conductive thin films described above deposited on or coupled to a substrate. The substrate can be conductive or non-conductive, transparent or opaque, and can be selected from glass, fused silica, quartz, a polymeric material or a semiconductor material. The ZITO thin film can be deposited by physical vapor deposition, e.g., sputtering including ion-assisted deposition (IAD), or chemical vapor deposition, e.g., metal-organic chemical vapor deposition (MOCVD).

In another aspect, the invention can provide a display device comprising an electrode component using any of the transparent conductive thin films described above. The electrode component can be an anode or a cathode. The electrode can comprise any of the transparent conductive thin films described above. The display device can be a liquid crystal display (LCD) device. In other embodiments, the display device can be an organic light-emitting device (OLED). In certain other embodiments, as can be practiced separately, this invention can be directed to a photovoltaic device.

In a further aspect, the invention can provide a compound of a formula:

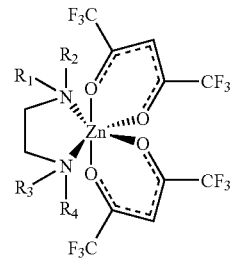

wherein $R_1$, $R_2$, $R_3$, and $R_4$ can be independently selected from H, a straight chain alkyl group, a branched chain alkyl group, a haloalkyl group, an alkenyl group and an alkynyl group. The compound can be used as a zinc precursor for preparing any of the thin films described above by MOCVD. In some embodiments, each of $R_1$, $R_2$, $R_3$, and $R_4$ can be a methyl group. In other embodiments, each of $R_1$, $R_2$, $R_3$, and $R_4$ can be an ethyl group. In further embodiments, each of $R_1$ and $R_3$ can be an ethyl group and each of $R_2$ and $R_4$ can be H. Alternatively, each of $R_1$ and $R_2$ can be an ethyl group and each of $R_3$ and $R_4$ can be H.

A further aspect of the invention can provide a method or process for increasing the conductivity of an indium oxide material. Such a method can comprise providing an indium oxide material and annealing the material at a pressure less than about 0.01 Torr and in a temperature range between about 400° C. and about 600° C. Alternatively, instead of annealing the material under the conditions described above, the material can be heated to a temperature greater than or equal to about 500° C. An inert gas such as argon or nitrogen can be passed over the heated material at about atmospheric pressure to increase the conductivity of the indium oxide material. The indium oxide material can be one of the ZITO thin films described above.

As can relate to various other aspects of this invention, it is an object of the present invention to provide a variety of anode components or structures, related electroluminescent articles/devices and/or method(s) for their use, production and/or assembly, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Accordingly, it is an object of the present invention to provide various alternatives to ITO materials for use in conjunction with electrode components, luminescent media and/or various electroluminescent devices, in particular transparent conducting oxides (TCOs) providing broader optical transparency windows, comparable or greater electrical conductivities and improved, higher work functions as compared to ITO and related semi-conductor materials or components of the prior art.

Other objects, features, benefits and advantages of the present invention will be apparent from this summary and its descriptions of various preferred embodiments, and will be readily apparent to those skilled in the art having knowledge of various electroluminescent devices and assembly/production techniques, together with the design and fabrication of related anode structures. Such objects, features, benefits and advantages will be apparent from the above as taken in conjunction with the accompanying examples, data, figures and all reasonable inferences to be drawn therefrom.

In part, the present invention is preferably embodied but not limited by the implementation of four new highly transparent, high work function thin film TCO materials as OLED anodes and related device structures: Ga—In—Sn—O (GITO), Zn—In—Sn—O (ZITO), Ga—In—O (GIO), and Zn—In—O (ZIO). Work function can be and is typically defined as the minimum energy needed to remove an electron from the Fermi level of a metal or metal composition, as expressed in electron volts (eV). Besides exhibiting high electrical conductivities (1000-3300 S/cm) and broad, outstanding optical transparencies (>90%), the present TCO films possess unusually high work functions (5.2-6.1 eV vs. ~4.7 eV for ITO). In particular, ZITO, having a work function of 6.1 eV, is the highest work function transparent anode material yet available for OLED fabrication. Conventional structure OLEDs fabricated with these anodes exhibit performance characteristics which differ in interesting, informative, and potentially useful ways from those of conventional ITO-based devices.

Accordingly, the present invention can be more broadly directed to an electroluminescent article or device including an anode fabricated from a TCO material of the type described herein. Such devices or articles together with various luminescent media or structural components can be designed and fabricated as described more fully in U.S. Pat. No. 5,834,100 and the patents cited therein, each of which are incorporated herein by reference in their entirety.

As such, the present invention can also be contemplated in a broader context so as to include an organic light-emitting diode device. Such a device comprises (1) an anode component comprising a metal conducting oxide material having a work function greater than 4.7 eV, (2) a cathode component, and (3) at least one organic conductive layer and/or component between the electrodes. A range of conducting oxide materials can be used with such a diode device, such materials as are currently known and available or as could be prepared using known synthetic techniques en route to the physical, functional and/or performance parameters described herein. Such considerations provide for use of a variety of Ga—In—O and Zn—In—O compositions over a range of stoichiometries. Preferred compositions include an Sn dopant. Sn-doped Zn—In—O compositions have been found especially useful, as described more fully herein. Without restriction to any one stoichiometric relationship, $Zn_{0.45}In_{0.88}Sn_{0.66}O_3$ is one such highly preferred composition given its work function alignment with the ionization potential of various organic compositions used in the fabrication of diode structures and devices.

As illustrated below, in several examples, such devices can be fabricated to include hole injection, hole transport, electron transport, electron injection and/or emissive layers, components and/or compositions. Such layers, components and/or compositions would be understood and known to those skilled in the art made aware of this invention, as would techniques relating to their preparation and inclusion in OLED device structures. However, as described more fully below, the present invention is demonstrated as especially useful in conjunction with blue light-emitting polymers and fabrication of the corresponding polymer light-emitting diodes. Without limitation, one such blue emitting polymer is poly(9,9-dioctylfluorene), the performance of which in a diode structure is significantly enhanced using one of several anode component materials of this invention.

As a corollary thereto, the present invention also includes a method of using a TCO material of the type described herein to improve, enhance or otherwise modify various anode properties and/or operating characteristics of OLED devices fabricated therewith, such properties and/or characteristics as discussed more fully below. More particularly, TCO materials, such as ZIO, GIO, GITO, and ZITO, exhibit high electrical conductivity, outstanding optical transparency, and work functions considerably greater than that of commercial ITO substrates. Optoelectric devices fabricated with such materials as anodes perform comparably or superior to ITO-based devices.

Accordingly, the present invention can also include an optoelectric anode component including a doped indium oxide composition having a work function greater than the reported value for ITO materials of the prior art. Preferably, such compositions have a work function greater than about 5.0 eV, such as can be obtained using either a Ga or Zn dopant, and providing the corresponding Ga—In—O and Zn—In—O compositions. Enchancement of various physical and/or functional characteristics and resulting performance properties can be realized with an anode component further including an Sn dopant, preferably providing a stoichiometric range of Ga—In—Sn—O and Zn—In—Sn—O compositions. Such an anode component is described herein and in the context of an OLED device, but use thereof can be extended as would be understood by those skilled in the art to other optoelectric devices. Alternatively, indium oxide can be doped with various other metal dopants such as but not limited to Sb, Pb, Ge, Al and Cd—the choice of which, amount and stoichiometry depending upon resulting work function. The corresponding doped compositions can be incorporated into an anode component as described more fully below.

In part, the present invention also includes one or more methods of using a TCO material of this invention and/or the doping thereof to reduce the energy difference between an anode comprising such a material and the highest occupied molecular orbital (HOMO) level of an associated OLED component. Such a difference is, at least in part, due to an improved work function and/or Fermi level position of the resulting anode relative to the energy level of a particular hole injection and/or emissive component, resulting in various performance properties of the type described herein. Such methods are effected by choice of an appropriate TCO material, anode fabrication and incorporation thereof into an OLED device.

As such, the present invention is also directed to a method of using energy level alignment to enhance the performance properties of an organic light-emitting diode device. Such a method includes (1) providing an anode component fabricated using a conductive oxide material, the material having a given work function; and (2) contacting the anode with a conductive layer component and/or composition having an ionization potential, the potential energy level aligned with the anode oxide work function level, such alignment defined by less than a 1.2 eV difference between the ionization potential and work function. For a particular conductive layer (e.g., hole injection, hole transfer, emissive, electron transfer and/or electron injection zones or components) an anode component and composition thereof can be designed to align corresponding energy levels. Alignment reduces the hole injection energy barrier of such a device and can be achieved through use of the present conductive oxide materials.

As a preferred embodiment, the present invention can also be considered in the context of conjugated polymer electroluminescence. Among the three primary colors, green and red polymer light-emitting diodes (PLEDs) have heretofor provided high brightness and quantum efficiency, while blue PLEDs have not previously demonstrated satisfactory performance for the purpose of display applications. Due to the high ionization potentials of most blue-emitting polymers, hole injection at the anode/polymer contact in a blue PLED is usually inefficient. For example, one of the most promising blue emitting polymers, poly(9,9-dioctylfluorene) (PFO), has a highest occupied molecular orbital (HOMO) level, or ionization potential, of 5.9 eV. Using a prior art indium-In-Oxide (ITO) (4.7 eV) as the anode, imposes a hole injection barrier of 1.2 eV.

Reducing the hole injection barrier is an integral step in the design of blue PLED devices, and one now available through the present invention. As mentioned earlier, the work function of a preferred zinc-indium-tin-oxide (ZITO) film is determined by ultra-violet photoelectron spectroscopy (UPS) to be 6.1 eV, which is significantly higher than that of ITO and aligns with the HOMO level (5.9 eV) of PFO. In a PLED device having ZITO as anode and PFO as emissive-layer (EL), the hole injection barrier is essentially overcome. As shown in the following examples, substituting ZITO for ITO as an anode material, in a PFO-based blue PLED device, provides a dramatic increase in device performance, as evidenced by a lower turn-on voltage, higher luminance, and higher quantum efficiency. Even so, as described herein, various other conductive layers, components and/or compositions can be utilized comparably with various other transparent conducting oxide materials of this invention.

The foregoing, and other features and advantages of the invention as well as the invention itself, will be more fully understood from the following figure, description, and claims.

BRIEF DESCRIPTION OF THE DRAWINGS

A skilled artisan will understand that the drawings described below are for illustration purposes only and are not necessarily to scale. The drawings are not intended to limit the scope of the present teachings in any way.

FIG. 4. A schematic illustration showing ITO and ZITO diode device structures and comparing anode work functions with the ionization potential of a blue light-emitting polymer, PFO.

FIGS. 5A-5C. Comparing the diodes illustrated in FIG. 4, ZITO or ITO/PFO/Ca/Al (ITO ● and ZITO ▲): 5A) Light output, 5B) external quantum efficiency and 5C) current voltage characteristics as a function of operating voltage.

DETAILED DESCRIPTION OF CERTAIN EMBODIMENTS

Figure 1:
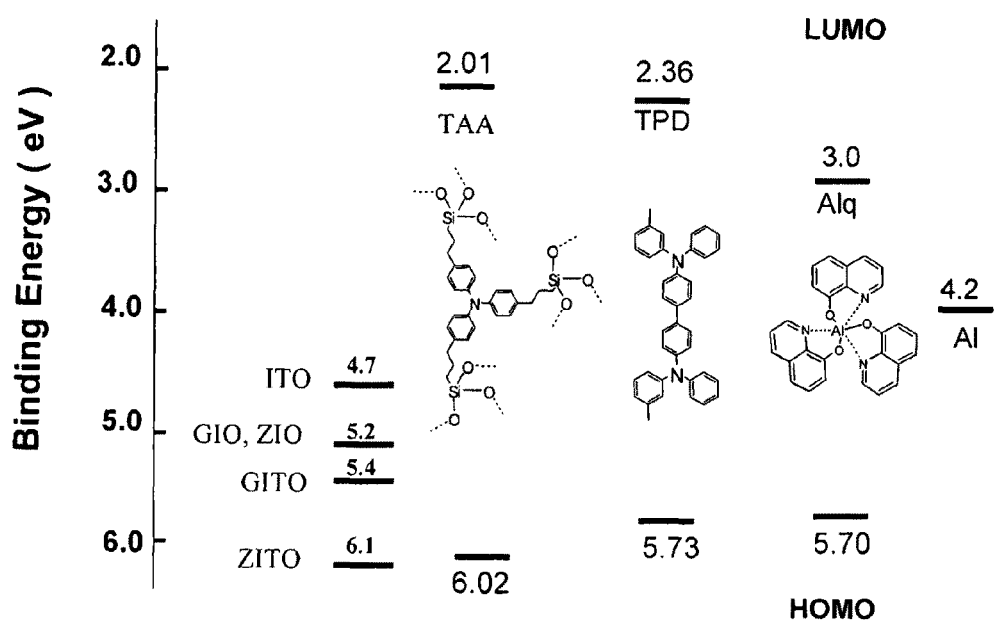
FIG. 1. Fermi level, HOMO/LUMO energy level alignment of the OLED components fabricated with various transparent conducting anode materials.

The present invention relates to transparent conductive thin films, processes for producing the same, and precursors for producing the same, as well as transparent, electroconductive substrate for display panels and organic electroluminescence devices that include such transparent conductive thin films.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. It should be understood that the order of steps or order for performing certain actions is immaterial so long as the invention remains operable. Moreover, two or more steps or actions may be conducted simultaneously.

Throughout the description, the use of the singular includes the plural (and vice versa) unless specifically stated otherwise. In addition, where the use of the term "about" is before a quantitative value, the present teachings also include the specific quantitative value itself, unless specifically stated otherwise.

1. Transparent Conductive Thin Film

Transparent conductive thin films of the invention are based on a zinc-indium-tin-oxide (ZITO) ternary system. Specifically, ZITO films of the invention are based on ZnO/SnO$_2$-cosubstituted In$_2$O$_3$. In certain embodiments, the ZITO films of the invention can be described by the formula: Zn$_w$In$_x$Sn$_y$O$_z$, wherein w=1, 1.5<x<4.0 and 0.5<y<2.5. Since the oxygen content varies from film to film, oxygen stoichiometry in the films is simply referred to as "z" in the formula, as is standard practice for other TCO materials.

In$_2$O$_3$ is a semiconductor with a band gap of about 3.75 eV and has a cubic bixbyite crystal structure where every fourth anion site is vacant. As prepared, In$_2$O$_3$ is usually non-stoichiometric (In$_2$O$_{3-\delta}$, $\delta$~0.01) due to oxygen vacancies which can act as doubly ionized donors and can contribute up to two electrons/vacancy to the conduction band. Depending on the deposition technique and substrate, the electrical conductivity of In$_2$O$_3$ thin films can vary from 300 S/cm to 4000 S/cm. The electrical and optical properties of In$_2$O$_3$ also can be altered by incorporating various dopants, such as Zn, Cd, Sn, and Ga.

The combinations of these dopants with In$_2$O$_3$ provide a broad array of new TCO materials to be studied and understood. Among them, the Zn—In—Sn—O (ZITO) system is particularly interesting. The solubility limit for SnO$_2$ in In$_2$O$_3$ has been established to be about 6 cation % for the bulk material, and the solubility of ZnO in In$_2$O$_3$ is even lower. However, when ZnO and SnO$_2$ are co-substituted into In$_2$O$_3$, their solubilities are increased. Nonetheless, previous studies have indicated that a minimum indium content of about 60 cation % is still required to retain the In$_2$O$_3$ bixbyite structure in bulk ZITO materials. While the ZITO system has been extensively studied in the bulk form, there have been relatively few studies of ZITO thin films.

It is therefore unexpected that ZITO thin films can be prepared with an indium content significantly lower than 60 cation % while retaining a bixbyite structure. It has been discovered that ZITO thin films of the invention have retained a phase-pure bixbyite structure with an indium content of as low as about 40 cation %, while demonstrating optical and electrical properties superior or comparable to ITO thin films. Specifically, the reduction in indium content has been accomplished by increasing the level of Sn doping substantially over its value in previous ITO and ZITO thin films. The decrease in indium content in ZITO thin films was surprisingly found to have a less than proportional effect on their conductivity. It also has been discovered that the conductivity of ZITO thin films can be increased by annealing. In terms of optical transmittance, the ZITO thin films of the invention were shown to be comparable to the range achieved by previous ITO and ZITO materials. Thus, ZITO thin films of the invention thus offer themselves as attractive alternatives to current commercial ITO films, especially in terms of material costs.

Accordingly, in one aspect, the invention relates to ZITO films having a relative tin (Sn) cation content [rcc(Sn)] greater than or equal to 10% and a conductivity greater than or equal to 2300 S/cm at room temperature (i.e., about 25° C.). In some embodiments, the ZITO thin films have a relative Sn cation content greater than 10%, greater than 20%, greater than 30%, or greater than 33%. In certain embodiments, the ZITO thin films have a relative indium (In) cation content [rcc(In)] less than 70%, less than 60%, less than 50%, less than 45%, or less than or equal to 44%.

In another aspect, the invention relates to ZITO films having a relative indium (In) cation content [rcc(In)] less than or equal to 45% and a conductivity greater than or equal to 2300 S/cm at room temperature (i.e., about 25° C.). In certain embodiments, the ZITO thin films have a relative In cation content less than or equal to about 40%.

As used herein, rcc(Zn)=w/(w+x+y), rcc(In)=x/(w+x+y) and rcc(Sn)=y/(w+x+y).

In certain embodiments, the ZITO films have a relative tin cation content greater than 33% and a relative indium cation content less than 40%, while maintaining a conductivity greater than or equal to 2300 S/cm at room temperature (i.e., about 25° C.). In some embodiments of the invention, the atomic ratio of tin to indium (Sn/In) in the ZITO thin films of the invention is between 0.40 and 1.00, more specifically, between 0.40 and 0.75, or between 0.75 and 1.00.

It is well known that both optical absorption and electrical conductivity increase with the thickness of a TCO film. To be useful in most commercial applications, it is typically required that TCO films have an absorption coefficient less than about 3000 cm$^{-1}$ in the visible range and an electrical conductivity greater than about 1000 S/cm. The thickness (e) of a commercially useful TCO film is therefore subjected to the antagonist constraints of a minimum optical transparency (T$_{min}$) and a maximum surface resistance (SR$_{max}$).

The ZITO thin films of the invention generally have a film thickness between about 100 nm and about 2000 nm. In some embodiments, the film thickness is less than or equal to 1000 nm. Within this thickness range, the ZITO thin films were found to have an average transmittance (T$_{avg}$) greater than or equal to about 80% between 400 nm and 1500 nm. For example, the thin films may have a light absorption coefficient less than 2700 cm$^{-1}$ at 550 nm. In certain embodiments, the thin films of the invention have a light absorption coefficient less than 2000 cm$^{-1}$ at 550 nm. As for conductivity, it was found that the thin films of the invention can have conductivity greater than or equal to 2300 S/cm at 25° C. In some embodiments, the thin films of the invention have conductivity greater than 1400 S/cm at 25° C., greater than 1700 S/cm at 25° C., greater than 2000 S/cm at 25° C., greater than 2500 S/cm at 25° C., greater than 2700 S/cm at 25° C., or greater than 2800 S/cm at 25° C. In certain embodiments, the conductivity is greater than or equal to 2900 S/cm at 25° C.

Some embodiments of the invention provide a TCO thin film with a prescribed optical transparency and/or a prescribed surface resistance that has a lower indium content than previous ITO and ZITO materials. ZITO thin films of the invention achieve these properties as described above. To quantify this particular advantage of the present invention, a variable Q representing the quotient of conductivity (S) and relative indium cation content [rcc(In)], i.e., $$Q = S/rcc(\text{In}),$$

may be used to compare among various ITO and ZITO TCO materials for a given minimum absorption coefficient. For some ZITO thin films, a Q value greater than or equal to 5300 can be achieved. In certain embodiments, Q can be as high as 6500.

In certain embodiments, the ZITO thin films are solid solutions of $In_2O_3$, $SnO_2$ and ZnO. As mentioned above, it was found that a phase-pure bixbyite structure can be retained in ZITO thin films with an indium content as low as about 40 cation %. It was found that Zn and Sn reach their solubility limit at about x=about 1.8 and y=about 1.7, and a second ZnO phase was detected in some embodiments.

Atomic force microscopy shows that the ZITO thin films can have satisfactory surface smoothness, with room-mean-square (RMS) roughness less than or equal to 2% of the film thickness. In certain embodiments, the RMS is less than or equal to 5 nm.

In addition to the desirable properties described above, ZITO thin films can also exhibit appreciable chemical inertness. It typically requires more than 1 hour to dissolve a 200 nm thick ZITO film in concentrated hydrochloric acid, while less than 15 minutes are required for a commercial 130 nm thick ITO film. Accordingly, ZITO thin films of the invention can offer multiple desirable properties compared to previous ITO and ZITO materials.

2. Processes for Producing Transparent Conducting Oxide Thin Films

Various deposition processes have been used to produce TCO thin films. They include various physical and chemical deposition techniques. Non-limiting examples of physical deposition techniques include sputtering, pulsed laser deposition and vacuum evaporation. Examples of chemical deposition techniques include, but are not limited to, ion plating and chemical vapor deposition such as metal-organic chemical vapor deposition (MOCVD) and plasma enhanced chemical vapor deposition (PECVD). Non-limiting examples of deposition processes that involve a mixture of chemical and physical means include reactive sputtering and molecular beam epitaxy (MBE).

Sputtering is an effective process for forming a film of a compound of low vapor pressure on a substrate, or forming a film whose thickness needs to be precisely controlled. It has been widely used because of its relatively simple procedures. Typically, a gaseous plasma is generated in a vacuum chamber to provide energetic ions. These ions bombard against the surface of a solid target and eject its atoms into the gas phase. Film growth is achieved by deposition of the sputtered atoms on the substrate.

Sputtering is categorized by the method used to produce the gaseous plasma. Radio-frequency (RF) sputtering (when radio-frequency plasma is used) and direct-current (dc) sputtering (when dc plasma is used) are the most common. A third method known as magnetron sputtering produces thin films by focusing the gaseous plasma immediately above the target by a magnet provided on the backside of the target. This method can have high ion collision efficiency even at low gas pressure. A further sputtering technique is known as ion-assisted deposition (IAD). In this method, the substrate is exposed to a secondary ion beam that operates at a lower power than the sputter gun. ZITO thin films produced by sputtering typically have excellent surface smoothness and tend to be amorphous in structure.

MOCVD is an attractive growth process for oxide thin films because it offers good compositional control, simple equipment, conformal coverage, and it can be readily scaled up for large-area depositions. It is also possible to grow ZITO films having metastable phases which do not exist in standard phase diagrams via MOCVD techniques. A substrate is exposed to one or more volatile precursors, which react and/or decompose on the substrate surface to produce the desired TCO thin film.

Among the various reaction parameters associated with MOCVD, growth temperature and $O_2$ flow rate were found to have a pronounced effect on film properties. Certain of the ZITO thin films were grown over a temperature range of 350-535° C. It was found that when the growth temperature is below 420° C., the films tended to be largely amorphous and often opaque. Films deposited between 420-470° C. typically were crystalline, however the carbon content was high (>5%), due to incomplete decomposition of the organic species. It is believed that films deposited above 510° C. have very low Sn contents because the tin precursor used [Sn(acac)2] decomposed before reaching the reactor film growth area. Using the reactor described in Example 5, a good temperature window for ZITO film growth was found to be about 470-510° C., within which a temperature of about 500° C. was preferred. In general, higher temperatures can afford lower carbon contamination and higher crystallinity of deposited ZITO thin films.

In terms of $O_2$ flow rate, it was found that when the $O_2$ partial pressure was low, the deposited films usually were not transparent and were morphologically rough, possibly due to incomplete precursor decomposition. When the $O_2$ partial pressure was high, the charge carrier concentration and conductivity of the deposited films often were low, presumably due to filling of oxygen vacancies in the $In_2O_3$ matrix. An $O_2$ partial pressure of about 2.0-2.4 Torr was found to yield crystalline, transparent, smooth and conductive ZITO thin films.

The optical and electrical properties of as-grown TCO films often can be enhanced or compromised by various types of post-treatment. For example, previous studies have shown that reductive annealing has the undesirable effect of reducing the conductivity of ZITO films by more than 40% (see, e.g., Freeman et al. (2000), MRS Bulletin, 45-51). In another study of ZITO films, post-annealing in a reductive environment at temperatures between 300° C. and 450° C. yielded a less than 10% increase in conductivity (see, e.g., Phillips et al. (1995), *Appl. Phys. Lett.*, 67(15): 2246-2248).

It was therefore surprising to observe a significant increase in the conductivities of some ZITO thin films of the invention following annealing treatment in vacuum at high temperatures. More specifically, annealing an indium oxide material at a pressure less than or equal to about 0.01 Torr and in the temperature range between about 400° C. and about 600° C., increased the electrical conductivity of the indium oxide material by about 20-40%. Alternatively, a similar increase in conductivity may be achieved by heating an indium oxide material to a temperature greater than or equal to about 500°

C., and passing an inert gas (e.g., argon (Ar) or nitrogen (N2)) over the heated indium oxide material at about atmospheric pressure.

Any of the various deposition methods and post-treatment procedures described above can be used to prepare some of the ZITO thin films of the invention in addition to any other methods known by those skilled in the art. Substrates on which ZITO thin films can be deposited include conductive and non-conductive substrates such as glass, fused silica, quartz, various polymers, and various semiconductor materials. Transparent conductive substrates including the ZITO thin films of the invention are within the scope of the invention as are their preparation methods.

3. MOCVD Precursors

Another aspect of the invention is related to MOCVD precursors that can be used to prepare the ZITO thin films described above. Specifically, the invention provides a new series of thermally stable zinc diamine adducts that have improved volatility characteristics versus conventional zinc MOCVD precursors and their derivatives. Another advantage of the zinc diamine adducts of the invention is their simple synthesis and purification.

Generally, the precursors of the invention have the formula:

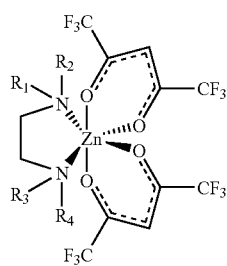

(I)

wherein $R_1$, $R_2$, $R_3$, and $R_4$ are independently selected from the group consisting of H, an alkyl group, a haloalkyl group, an alkenyl group and an alkynyl group. In some embodiments, $R_1$, $R_2$, $R_3$, and $R_4$ are independently selected from the group consisting of H, a $C_{1-10}$ alkyl group, a $C_{1-10}$ haloalkyl group, a $C_{2-10}$ alkenyl group and a $C_{2-10}$ alkynyl group.

As used herein, the term "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl) and the like. A lower alkyl group typically has up to 4 carbon atoms. Examples of lower alkyl groups include methyl, ethyl, propyl (e.g., n-propyl and isopropyl), and butyl groups (e.g., n-butyl, isobutyl, s-butyl, t-butyl).

As used herein, "alkenyl" refers to a straight-chain or branched alkyl group having one or more double carbon-carbon bonds. Examples of alkenyl groups include ethenyl, propenyl, butenyl, pentenyl, hexenyl, butadienyl, pentadienyl, hexadienyl groups, and the like. The one or more double carbon-carbon bonds may be internal (such as in 2-butene) or terminal (such as in 1-butene).

As used herein, "alkynyl" refers to a straight-chain or branched alkyl group having one or more triple carbon-carbon bonds. Examples of alkynyl groups include ethynyl, propynyl, butynyl, pentynyl, and the like. The one or more triple carbon-carbon bonds may be internal (such as in 2-butyne) or terminal (such as in 1-butyne).

As used herein, "haloalkyl" refers to an alkyl group having one or more halogen substituents. Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." As used herein, "halo" or "halogen" includes fluoro, chloro, bromo, and iodo.

Whenever substituents of compounds of the invention are disclosed in groups or in ranges, it is specifically intended that the invention include each and every individual subcombination of the members of such groups and ranges. For example, the term "C1-10 alkyl" is specifically intended to individually disclose $C_1$, $C_2$, $C_3$, $C_4$, $C_5$, $C_6$, $C_7$, $C_8$, $C_9$, $C_{10}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, and $C_9$-$C_{10}$ alkyl.

In one embodiment, each of $R_1$, $R_2$, $R_3$, and $R_4$ is a methyl group. In another embodiment, each of $R_1$, $R_2$, $R_3$, and $R_4$ is an ethyl group. In yet another embodiment, each of $R_1$ and $R_3$ is an ethyl group and each of $R_2$ and $R_4$ is H. In a further embodiment, each of $R_1$ and $R_2$ is an ethyl group and each of $R_3$ and $R_4$ is H. The chemical names of the compounds described immediately above are bis(1,1,1,5,5,5-hexafluoro-2,4-petanedionato)(N,N,N',N'-tetramethylethylenediamine) zinc [Zn(hfa)$_2$(TMEDA)], bis(1,1,1,5,5,5-hexafluoro-2,4-pentanedionato)(N,N,N',N'-tetraethylethylenediamine)zinc [Zn(hfa)$_2$(TEEDA)], bis(1,1,1,5,5,5-hexafluoro-2,4-pentanedionato)(N,N'-diethylethylenediamine)zinc [Zn(hfa)$_2$(N,N'-DEA)], and bis(1,1,1,5,5,5-hexafluoro-2,4-pentanedionato)(N,N-diethylethylenediamine)zinc [Zn(hfa)$_2$(N,N-DEA)], respectively.

The zinc MOCVD precursors of the invention can be prepared in a straightforward single-step aqueous phase reaction under ambient conditions from commercially available reagents as described in Example 10 below. The products are insoluble in the reaction solution and can be isolated by filtration. The complexes can be further purified by sublimation under reduced pressure typically to yield white crystalline solids. Qualitatively, these complexes are found to be more volatile than current-generation Zn precursors, and are air- and moisture-stable. Particularly, the melting temperature range of at least one of the above-identified precursors is as low as about 64-66° C. Consequently, these precursors satisfy certain criteria to be effectively used to prepare ZITO thin films of the invention.

4. Transparent Conductive Substrate for Display Panels

Yet another aspect of the present teachings includes a transparent, electroconductive substrate for display panels that includes a ZITO thin film of the invention formed on a substrate selected from the group consisting of a glass substrate, a quartz plate, a polymeric material such as a resin plate or film, and a semiconductor material. A transparent, electroconductive substrate can function as the anode and/or cathode of the display panel. Examples of display panels include, but are not limited to, liquid crystal displays (LCDs), plasma display panels (PDPs), and electroluminescent (EL) devices. Incorporation of a transparent, electroconductive substrate into any of these display panels preferably does not require modification of the construction of the panels. Instead, the conventional transparent electrode(s) in the panel is substituted by the transparent, electroconductive substrate of the invention. The resulting display panel enjoys improved performance due to greater conductivity, enhanced transparency and more realistic color display, especially in the blue portion of the visible spectrum, conferred by the transparent, electroconductive substrate of the invention.

5. Transparent Conducting Oxide Thin Films for Light-Emitting Diodes

The present teachings further relate to an electroluminescent (EL) article or device, e.g., an organic light-emitting diode (OLED) device, that includes an anode fabricated from a ZITO thin film of the invention. In addition to the anode including a ZITO thin film, such a device typically also includes a cathode component and at least one organic conductive layer between the electrodes. One or more of such organic conductive layers may function as a hole injection layer, a hole transport layer, an electron transport layer, an electron injection layer, and/or an emissive layer. By substituting a ZITO thin film for the conventional ITO film as an anode material, the EL device may exhibit improved device performance as evidenced by a lower turn-on voltage, higher luminance, and/or higher quantum efficiency.

The following examples are provided to illustrate further and to facilitate the understanding of the invention and are not in any way intended to limit the invention.

EXAMPLES OF THE INVENTION

The following non-limiting examples and data illustrate various aspects and features relating to the conducting oxide materials, anodes and/or devices of the present invention, including improved anode conductivities and work functions, as are available through use of the TCO materials described herein. Such aspects and features are described in more detail, hereafter. In comparison with the prior art, the present materials, anodes and articles/devices provide results and data which are surprising, unexpected and contrary to the prior art. While the utility of this invention is illustrated through the use of several TCO materials and related anode structures fabricated therewith, it will be understood by those skilled in the art that comparable results are obtainable with various other TCO materials, components and anode structures, as are commensurate with the scope of this invention.

Likewise, without limitation, the present invention can be described and illustrated by four representative TCO materials, each of which can be prepared, isolated and/or characterized as described in the prior art:

GITO: A. Wang, N. L. Edleman, J. R. Babcock, T. J. Marks, M. A. Lane, P. W. Brazin, C. R. Kannewurf, *Mat. Res. Soc. Symp. Proc.* 2000, 607, 345; A. J. Freeman, K. R. Poeppelmeier, T. D. Mason, R. P. H. Chang, T. J. Marks, *MRS Bull.* 2000, 25, 45.

ZITO: A. Wang, N. L. Edleman, J. R. Babcock, T. J. Marks, M. A. Lane, P. W. Brazis, C. R. Kannewurf, *Mater. Res. Soc. Symp. Proc.* 2000, 607, 345. A. J. Freeman, K. R. Poeppelmeier, T. D. Mason, R. P. H. Chang, T. J. Marks, *MRS Bull.* 2000, 25, 45;

GIO: A. Wang, S. C. Cheng, J. A. Belot, R. J. Mcneely, J. Cheng, B. Marcordes, T. J. Marks, J. Y. Dai, R. P. H. Chang, J. L. Schindler, M. P. Chudzik, C. R. Kannewurf, *Mat. Res. Soc. Symp. Proc.* 1998, 495, 3; and ZIO: A. Wang, J. Dai, J. C. Cheng, M. P. Chudzik, T. J. Marks, R. P. H. Chang, C. R. Kannewurf, *Appl. Phys. Lett.* 1998, 73, 327. A. Wang, S. C. Cheng, J. A. Belot, R. J. Mcneely, J. Cheng, B. Marcordes, T. J. Marks, J. Y. Dai, R. P. H. Chang, J. L. Schindler, M. P. Chudzik, C. R. Kannewurf, *Mat. Res. Soc. Symp. Proc.* 1998, 495, 3. Y. Yan, S. J. Pennycook, J. Dai, R. P. H. Chang, A. Wang, T. J. Marks, *Appl. Phys. Lett.* 1998, 73, 2585.

Example 1

Growth conditions (MOCVD) on float glass substrates and characterization of ZITO, ZIO, GITO, and GIO thin films by X-ray diffraction, SEM, TEM, and AFM, as well as by other compositional, electrical, and microstructural techniques have been described previously. Microstructurally, all have homogeneously doped cubic $In_2O_3$ bixbyite crystal structures, and surface rms roughnesses comparable to commercial ITO. Effective work functions were determined by UV spectroscopy using the 21.8 eV He (I) source (Omicron H1513) of a Kratos Axis-Ultra 165 photoelectron spectrometer. (R. Schlaf, B. A. Parkinson, P. A. Lee, K. W. Nebesny, N. R. Armstrong, *Appl. Phys. Lett.* 1998, 73, 1026.) Work functions were obtained by lightly sputtering the TCO surface with an $Ar^+$ beam (1 keV), to remove adventitious impurities (as revealed by XPS) and then recording the difference in energy between the high kinetic energy onset and the low kinetic energy cutoff for photoionization. Samples were biased at −5 V to enhance the slope of the low kinetic energy cutoff region. Estimates of the high kinetic energy onset for photoionization were obtained by extrapolation of the high kinetic energy portion of the photoemission spectrum to the zero count baseline. The work function determined here for commercial ITO, 4.7 eV, is in the range typically reported. (R. Schlaf, B. A. Parkinson, P. A. Lee, K. W. Nebesny, N. R. Armstrong, *Appl. Phys. Lett.* 1998, 73, 1026.)

Example 2

Relevant properties of several TCO anodes of this invention are summarized in Table 1, below. Note that all have lower optical absorption coefficients than commercial ITO (Donelley Corp., 20Ω/□). The visible transparency windows of these films are also significantly broader than that of ITO. (A. Wang, N. L. Edleman, J. R. Babcock, T. J. Marks, M. A. Lane, P. W. Brazis, C. R. Kannewurf, *Mater. Res. Soc. Symp. Proc.* 2000, 607, 345.) Although ZIO and GIO have somewhat lower n-type conductivities (700-1000 S/cm) than commercial ITO (~3000 S/cm), the Sn-doped versions (GITO, ZITO) exhibit comparable values (2000-3300 S/cm). As currently understood, GITO and ZITO are the most transparent and among the most conductive TCO materials available for OLED fabrication. In terms of robustness, all of the present films are more chemically, inert than commercial ITO; e.g., to remove a 120 nm thick ITO film using 20% aqueous HCl at 25° C. requires ~5 min, while comparable degradation of GITO or GIO films requires ~4× longer. FIG. 1 summarizes TCO work function data and Fermi level positions relative to the energy levels of the components to be used in OLED fabrication (vide infra): the HOMOs of a crosslinked triarylamine (TAA) adhesion/injection layer and TPD hole transport layer (HTL), as well as the LUMO of the aluminum tris-quinoxalate (Alq) electron transport layer (ETL). (H. Ishii, K. Sugiyama, E. Ito, K. Seki, *Adv. Mater.* 1999, 11, 605.) These data are a measure of the intrinsic hole injection barrier, i.e., the energy offset between the organic HOMO level and the TCO Fermi level, in absence of other interfacial structural or electronic barriers. (H. Ishii, K. Sugiyama, E. Ito, K. Seki, *Adv. Mater.* 1999, 11, 605.) Note that all the present non-ITO TCO materials have work functions significantly greater than that of commercial ITO—indeed, the work function of the GITO films rivals that of Au (5.4 eV) while the value of ZITO (6.1 eV) is greater than that of Pt (5.7 eV). S. M. Sze, *Physics of Semiconductor Devices*, Wiley, N.Y. 1981.

TABLE 1

Physical Properties of TCO Anode Films on Glass Substrates.

| Anode Material [reference] | Thickness (nm) | Sheet Resistance ($\Omega/\square$) | Conductivity (S/cm) | Absorption Coefficient (cm$^{-1}$) (at 550 nm) | Work Function (eV) |
|---|---|---|---|---|---|
| $Ga_{0.12}In_{1.88}O_3$ | 1020 | 14 | 700 | 1100 | 5.2 |
| $Ga_{0.08}In_{1.28}Sn_{0.64}O_3$ | 170 | 18 | 3280 | 2000 | 5.4 |
| $Zn_{0.5}In_{1.5}O_3$ | 250 | 39 | 1030 | 800 | 5.2 |
| $Zn_{0.45}In_{0.88}Sn_{0.66}O_3$ | 360 | 12 | 2290 | 2700 | 6.1 |
| ITO[a] | 180 | 20 | 3500 | 8075 | 4.7 |

[a]ITO received from Donelley Corp., 20 $\Omega/\square$; other anode materials available and/or prepared as described above.

Example 3

Figure 2:
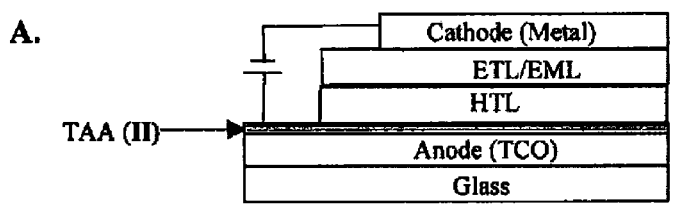
FIGS. 2A-2B. 2A) Structure of a three layer OLED, 2B) Structures of OLED molecular components. Upon spin-coating, precursor I hydrolyzes and crosslinks to form hole injection/adhesion layer II.
Figure 2:
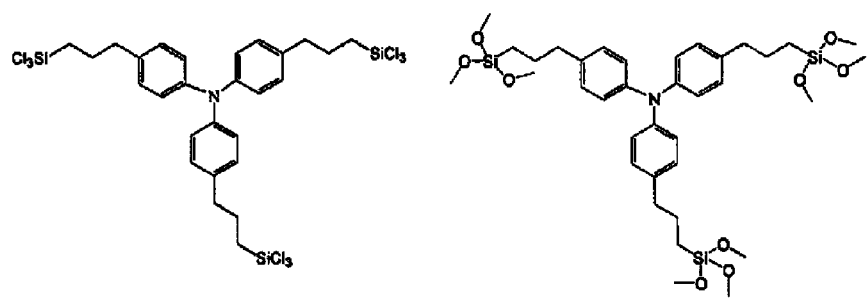
Figure 2:
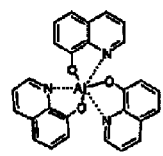
Figure 2:
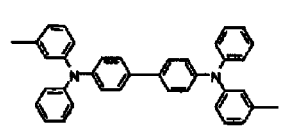

For OLED fabrication, the as-grown TCO and commercial ITO films were subjected to identical sequential cleaning with HPLC grade acetone, isopropanol, and methanol, then with an oxygen plasma to eliminate organic residues. All of the freshly cleaned metal oxide surfaces are highly hydrophilic as evidenced by advancing aqueous contact angles of ~0°. A thin, crosslinked TAA layer derived from N(4-$C_6H_4CH_2CH_2CH_2SiCl_3)_3$ (I, FIG. 2) was then spin-coated onto each of the anode surfaces from a 1 mM toluene solution and cured at 120° C. for 1.0 hour. This layer has been shown in previous work to enhance TCO/HTL interfacial cohesion and charge injection efficiency. The TAA films are robust, adherent, contiguous, and electroactive, with ~1.5 nm RMS roughness on all TCO substrates, and having a thickness of ~15 nm (by X-ray reflectivity.) (W. Li, J. E. Malinsky, H. Chou, W. Ma, L. Geng, T. J. Marks, G. E. Jabbour, S. E. Shaheen, B. Kippelen, N. Pegyhambarian, A. J. R. P. Dutta, J. Anderson, P. Lee, N. Armstrong, *Polymer Preprints*. 1998, 39, 1083.) Subsequent vacuum deposition (5×10$^{-6}$ Torr) of 50 nm of N,N'-diphenyl-N,N'-bis(3-methylphenyl)-1,1'-biphenyl-4-4' diamine (TPD) and 60 nm of gradient-sublimed aluminum tris-quinoxalate (Alq), followed by 100 nm of Al completed device fabrication (FIG. 2A.). The OLEDs were characterized inside a sealed aluminum sample container under a dry nitrogen atmosphere. A Keithley 2400 source meter supplied d.c. voltage to the devices and simultaneously recorded the current flow. Simultaneously, an IL 1700 research radiometer with calibrated Si photodetector was used to collect the photon emission. These instruments were controlled by a PC via LabView software.

Example 4

Figure 3:
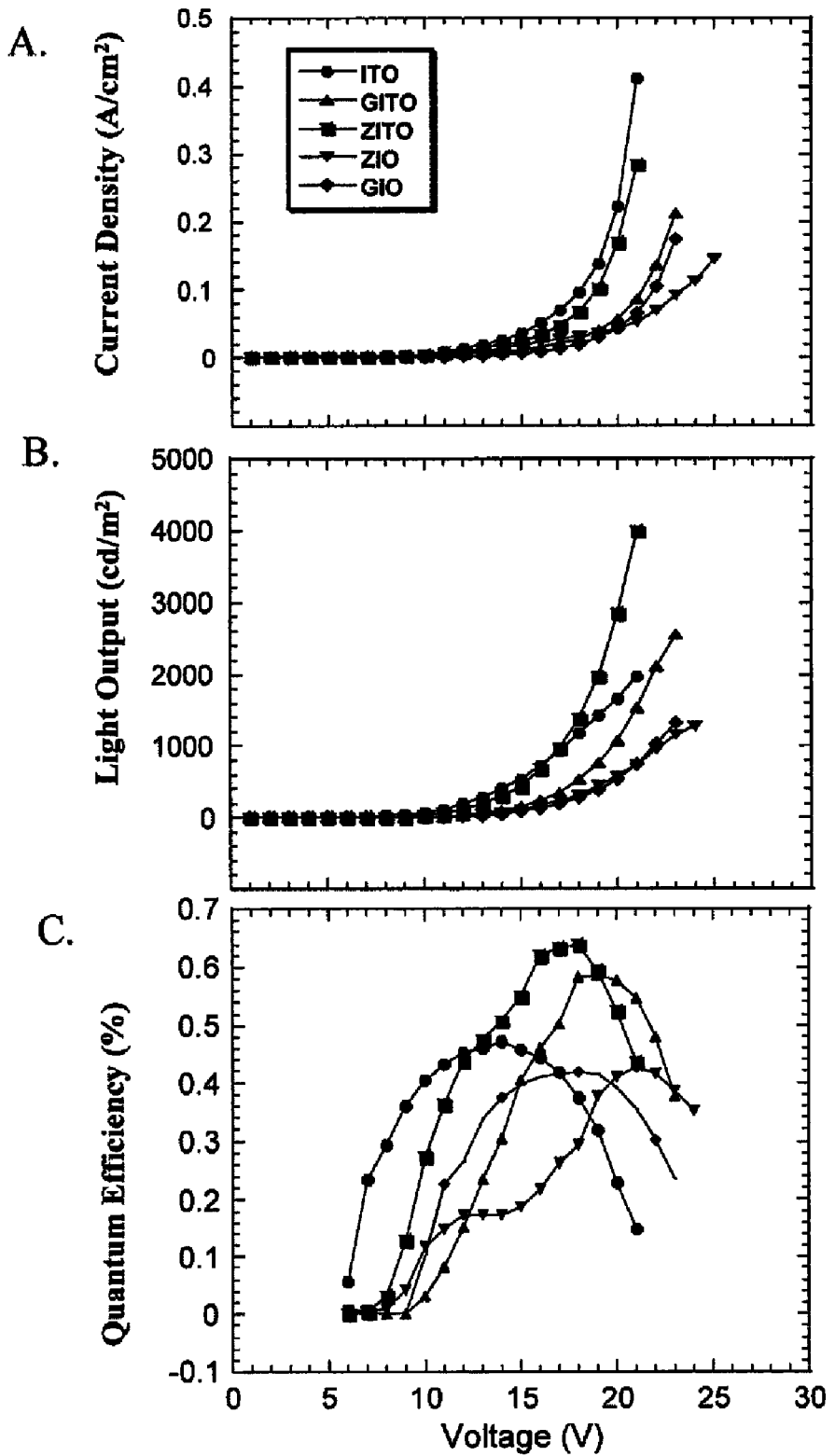
FIGS. 3A-3C. A. Current density, B. Luminescence, and C. External quantum efficiency as a function of bias for TCO/TAA/TPD/Alq/Al OLED devices fabricated with the indicated transparent conducting oxide anodes and with commercial ITO.

The operating characteristics of OLED devices fabricated, as described in the preceding example, with the present TCO and ITO anodes are compared and illustrated in FIG. 3. All show typical diode behavior with no current drawn in reverse bias, and in all cases, light turn-on occurs simultaneously with current turn-on. Within the 1.0 cd/m$^2$ photon detector resolution, the threshold voltage for light output varies significantly among the devices: 6.0 V for ITO, and 7.5, 9.0, 10.0, and 10.0 V for ZITO, ZIO, GITO, and GIO, respectively (Table 2, below). Regarding maximum light output, a brightness of ~1400 cd/m$^2$ is obtained for the GIO- and ZIO-based devices. While the GITO-based device has a maximum light output comparable to that of the ITO-based device (~2500 cd/m$^2$ at 22 V), the ZITO-based device exhibits a maximum brightness ~80% greater than the ITO-based device. At 21 V, a maximum brightness of 4000 cd/m$^2$ is observed for ZITO-based device at a current density corresponding to ~0.7× the value for the ITO-based device. Remarkably, at high driving voltages, which should be a measure of durability under extended use/stress, the forward quantum efficiencies of the ZITO- and GITO-based OLEDs (~0.6%) far exceed that of the present ITO-based OLED (~0.3%).

TABLE 2

Operating characteristics of OLED devices fabricated with various TCO anodes.

| Anode Material | [a]Turn-on Voltage (V) | Current Density at 100 cd/m$^2$ (mA/cm$^2$) | Light Output at 15 V (cd/m$^2$) | Maximum Forward Light Output (cd/m$^2$) | Maximum External Quantum Efficiency (%) |
|---|---|---|---|---|---|
| $Ga_{0.12}In_{1.88}O_3$ | 10 | 9.5 | 80 | 1320 | 0.4 |
| $Ga_{0.08}In_{1.28}Sn_{0.64}O_3$ | 10 | 9.7 | 150 | 2560 | 0.6 |
| $Zn_{0.5}In_{1.5}O_3$ | 9 | 19 | 110 | 1290 | 0.4 |
| $Zn_{0.45}In_{0.88}Sn_{0.66}O_3$ | 8 | 8.3 | 430 | 4000 | 0.6 |
| ITO | 6 | 8.5 | 540 | 1960 | 0.5 |

[a]Defined as the voltage at which 1 cd/m$^2$ light output is detected.

Example 5

Regarding OLED efficiency as a function of anode composition, it can be seen that Sn doping of the Ga—In—O and Zn—In—O systems substantially increases the conductivity, increases the work function, and yields superior OLED anodes. Note that the quantum efficiency and maximum light output of the GITO- and ZITO-based devices significantly exceeds that of the corresponding GIO- and ZIO-based devices, respectively. Apart from compositional differences, differences in work function among the new TCO materials should also be reflected in the respective OLED device performance, and indeed, within the GIO, ZIO, GITO, ZITO series, the apparent hole injection facility at moderate biases approximately tracks work function (Table 2, FIG. 3B), ZITO>GITO>ZIO~GIO. In the case of ZITO, hole injection from the ZITO anode into the proximate TAA layer should be energetically quite favorable due to the high ZITO work function, which lies significantly below the TAA HOMO level (FIG. 1). All other things being equal, the intrinsic hole injection barrier should be smaller for the ZITO/TAA interface than for the ITO/TAA interface, hence more efficient charge injection would be expected in ZITO-based devices. However, other factors appear operative. (FIG. 3). Although ITO has a 4.7 eV work function and a substantial estimated intrinsic hole injection barrier of ~1.3 eV with respect to the TAA HOMO, the ITO-based device nevertheless exhibits ~1.5 V lower turn-on voltage than the ZITO-based device and higher quantum efficiencies at low voltages. The lower conductivities of other TCOs (Table 1) cannot be invoked to explain these results, considering that the range of respective sheet resistances (12Ω/□-39Ω/□) spans that of ITO, and should not lead to a large voltage drop across the TCO surface. Likewise, improved charge injection balance (J. E. Malinsky, G. E. Jabbour, S. E. Shaheen, J. D. Anderson, A. G. Richter, N. R. Armstrong, B. Kipplelen, P. Dutta, N. Peyghambarian, T. J. Marks, *Adv. Mater.* 1999, 11, 227) via attenuation of hole injection cannot alone explain these results, since all other factors being equal, ZITO should inject holes more efficiently than ITO due to the lower intrinsic barrier, meaning all other factors being equal, a greater number of photonically unproductive holes should reach the cathode, resulting in a lower quantum efficiency. Note here, however, that the ZITO device operates at higher quantum efficiencies at high voltage ranges (FIG. 3C). Control experiments argue that anode growth technique is not a major factor since devices fabricated with MOCVD-derived ITO anodes exhibit quantum efficiencies comparable to those of devices fabricated with commercial ITO with slightly diminished turn-on voltages.

Example 6

The chemical structure of PFO is shown in FIG. 4. The polymer was synthesized via a Suzuki coupling reaction and was carefully purified to remove ionic impurities and catalyst residues. The number and weight average molecular weights ($M_n$ and $M_w$) of PFO were determined to be 54,700 and 106,975 (polydispersity=1.95), respectively, by gel permeation chromatography (GPC) using tetrahydrofuran as the solvent and polystyrene as the standard. ITO or ZITO coated glass was used as the substrate for PLEDs device fabrication. The substrates were first washed with methanol, iso-propanol, and acetone in an ultrasonic bath, dried in a vacuum oven, and then cleaned by oxygen plasma etching. PFO was spincast on the substrates from a xylene solution to give an emissive layer of a thickness about 80 nm. The resulting films were dried in a vacuum oven overnight. Inside an inert atmosphere glove box, calcium was thermally evaporated onto the PFO films over a base pressure $<10^{-6}$ Torr using a shadow mask to define 10 mm$^2$ electrode area, followed by aluminum deposition as a protection layer. The PLED devices were characterized inside a sealed aluminum sample container using instrumentation described elsewhere.

Example 7

The PLED devices fabricated in the preceding example were compared. The device characteristics of the ITO and ZITO PLED devices are shown in FIGS. 5A-C, respectively, for comparison of luminance-voltage(L-V), external quantum efficiency-voltage, and current-voltage(I-V). It can be clearly seen that the ZITO-based PLED device shows dramatic increase in charge carrier injection, brightness, and quantum efficiency compared to the ITO-based device; it turns on at about 8 V and reaches maximum luminance of about 2200 cd/m$^2$ at about 13 V and with an external quantum efficiency of 0.337%, while the ITO based device turns on at 12 V and reaches maximum luminance of about 200 cd/m$^2$ at 21 V and with an external quantum efficiency of 0.01%.

Example 8

Other PLED devices of this invention can be fabricated to include one or more additional organic layers and/or components of the prior art, such as but not limited to a hole injection layer and a hole transport layer. Illustrating the former is a triarylaminesiloxane (TAA) of the sort described above which can be fabricated using molecular self-assembly techniques. Various thiophene polymers can be spincast. With regard to a hole transport layer, known compositions of the prior art—irrespective of fabrication technique—can be utilized with good effect. In one such embodiment, TPD can be vapor deposited or silane funtionalized and applied via molecular self-assembly techniques. Such layer, roughened—as would be understood by those skilled in the art, can be used to further improve the performance enhancement demonstrated herein.

As provided above, anode work function is an important contributing factor in determining OLED hole injection barrier and device performance. However, other factors can be considered in conjunction therewith. For instance, for microstructurally very similar materials, anode work function is one variable governing OLED charge injection and exciton recombination efficiency, and can be considered with other variables such as electrode surface morphology, composition, and surface electronic states. Even so, the intrinsically high work function TCO materials and anodes of this invention can be used as described, above, for hole-limited OLEDs, or oxidation-resistant, atmospherically stable OLEDs for which energetic alignment with low-lying HOMO levels of organic layers and high work functions of air-stable cathodes are required. Furthermore, preliminary studies of device operational stabilities by biasing the devices under constant dc voltage reveal that OLEDs fabricated with the present non-ITO TCOs exhibit significantly higher stabilities ($\geq$2× longer luminescence decay half-lives) than commercial ITO-based devices.

Example 9

Indium oxide is doped, alternatively, with Sb, Pb, Ge, Al or Cd to provide the corresponding composition, over a range of stoichiometries. Such compositions can be, as further required by work function and hole injection barrier considerations, in turn doped with varying amounts of Sn. The preparation of such compositions can be achieved using techniques of the prior art, references to which are provided above and incorporated herein, or through straight-forward modifications thereof as would be understood by those skilled in the art and made aware of this invention.

Example 10

Preparation of zinc MOCVD precursors. Four Zn(hfa)2·diamine complexes, in which the diamine ancillary ligands were varied in symmetry and lipophilicity, were synthesized in a single-step reaction under ambient conditions from commercially available reagents as detailed below (Scheme 1). The products were insoluble in the H$_2$O/ethanol reaction solution and were isolated by filtration. The complexes were then purified by sublimation under reduced pressure to yield white crystalline solids. Qualitatively, these complexes were found to be more volatile than current-generation Zn precursors, and were air- and moisture-stable. Melting point data are summarized in Table 3, and NMR data are included in Examples 10a-10d below.

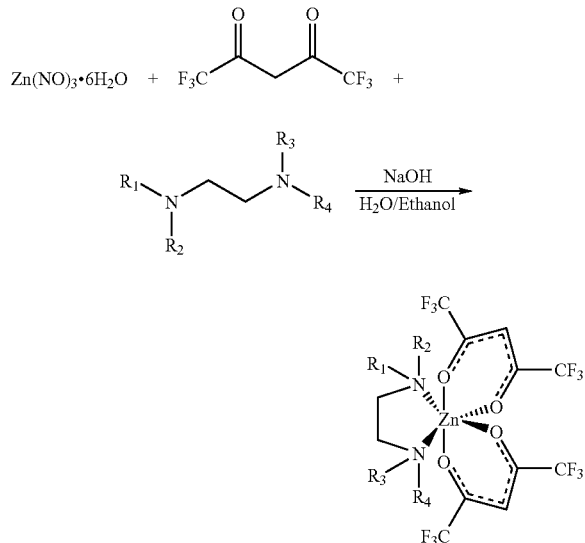

Scheme 1. Synthesis of Zn(hfa)2·diamine complexes

Example 10a

Synthesis of bis(1,1,1,5,5,5-hexafluoro-2,4-petanedionato)(N,N,N',N'-tetramethylethylenediamine) zinc, $Zn(hfa)_2(TMEDA)$ (1)

To 1.00 g (3.36 mmol) $Zn(NO_3)_2 \cdot 6H_2O$ dissolved in 60 mL deionized water was added 0.39 g (3.36 mmol) N,N,N',N'-tetramethylethylenediamine. Next, 1.40 g (6.72 mmol) 1,1,1,5,5,5-hexafluoro-2,4-pentanedione (Hhfa) was dissolved in 15 mL absolute ethanol. To the ethanol solution, 0.40 g (6.72 mmol) 1-propylamine was added dropwise over a period of 10 min. The ethanol solution was then slowly poured into the stirring Zn solution. The reaction mixture was stirred overnight and the crude product collected by filtration. The resulting white solid was dried over $P_2O_5$ and sublimed at 80° C./$10^{-5}$ Torr.

Yield: 1.26 g (63.2%). mp: 106-108° C. Anal. Calcd. for $C_{16}H_{18}O_4N_2F_{12}Zn$: C, 32.26; H, 3.05; N, 4.70. Found: C, 32.11; H, 2.98; N, 4.60. $^1$H NMR ($C_6D_6$, δ): 1.61 (s, 4H, $CH_2$), 1.79 (s, 12H, $CH_3$), 6.22 (s, 2H, COCHCO). $^{13}$C NMR ($C_6D_6$, δ): 45.28 ($CH_3$), 46.17 ($NCH_2CH_2N$), 89.17 (CH), 118.68 (q, J=286.3, Hz, $CF_3$), 178.89 (q, J=33.6 Hz, CO).

Example 10b

Synthesis of bis(1,1,1,5,5,5-hexafluoro-2,4-petanedionato)(N,N,N',N'-tetraethylethylenediamine)zinc, $Zn(hfa)_2(TEEDA)$ (2)

This compound was synthesized and purified via an approach similar to that for 1, starting with 1.00 g (3.36 mmol) $Zn(NO_3)_2 \cdot 6H_2O$, 1.40 g (6.72 mmol) Hhfa, 0.40 g (6.72 mmol) 1-propylamine, and 0.58 g (3.36 mmol) N,N,N',N'-tetraethylethylenediamine.

Yield: 1.36 g (62.2%). mp: 103-106° C. Anal. Calcd. for $C_{20}H_{26}O_4N_2F_{12}Zn$: C, 36.85; H, 4.02; N, 4.30. Found: C, 36.77; H, 3.76; N, 4.33. 1H NMR ($C_6D_6$, δ): 0.66 (t, 12H, $CH_3$), 1.92 (s, $NCH_2CH_2N$), 2.06 (m, 4H, $CH_3CH_aH_b$), 2.80 (m, 4H, $CH_3CHaH_b$), 6.26 (s, 2H, COCHCO). $^{13}$C NMR ($C_6D_6$, δ): 7.31 ($CH_3$), 38.34 ($CH_3CH_2$), 46.67 ($NCH_2CH_2N$), 88.46 (CH), 117.92 (q, J=286.1, Hz, $CF_3$), 179.15 (q, J=33.7 Hz, CO).

Example 10c

Synthesis of bis(1,1,1,5,5,5-hexafluoro-2,4-pentanedionato)(N,N'-diethylethylenediamine)zinc, Zn(hfa)2(N,N'-DEA) (3)

This compound was synthesized and purified via an approach similar to that for 1, starting with 1.00 g (3.36 mmol) $Zn(NO_3)_2 \cdot 6H_2O$, 1.40 g (6.72 mmol) Hhfa, 0.40 g (6.72 mmol) 1-propylamine, and 0.39 g (3.36 mmol) N,N'-diethylethylenediamine.

TABLE 3

Substitutions and melting points of $Zn(hfa)_2$ diamine complexes

| Abbreviations | $R_1$ | $R_2$ | $R_3$ | $R_4$ | Melting Point (° C.) |
|---|---|---|---|---|---|
| $Zn(hfa)_2(TEMDA)$ (1) | $CH_3$ | $CH_3$ | $CH_3$ | $CH_3$ | 106-108 |
| $Zn(hfa)_2(TEEDA)$ (2) | $CH_2CH_3$ | $CH_2CH_3$ | $CH_2CH_3$ | $CH_2CH_3$ | 103-106 |
| $Zn(hfa)_2(N,N'-DEA)$ (3) | $CH_2CH_3$ | H | $CH_2CH_3$ | H | 64-66 |
| $Zn(hfa)_2(N,N-DEA)$ (4) | $CH_2CH_3$ | $CH_2CH_3$ | H | H | 136-139 |

Yield: 1.34 g (66.9%). mp: 64-66° C. Anal. Calcd. for $C_{16}H_{18}O_4N_2F_{12}Zn$: C, 32.26; H, 3.05; N, 4.70. Found: C, 32.17; H, 2.96; N, 4.65. $^1$H NMR (C6D6, δ): 0.56 (t, 6H, $CH_3$), 1.07 (br s, 2H, NH), 1.63 (br s, 2H, $CH_3CH_aH_b$), 1.93 (br s, 4H, $NCH_2CH_2N$), 2.48 (br s, 2H, $CH_3CH_aH_b$), 6.24 (s, 2H, COCHCO). $^{13}$C NMR ($C_6D_6$, δ): 13.33 ($CH_3$), 44.20 ($CH_3CH_2$), 46.10 ($NCH_2CH_2N$), 89.57 (CH), 118.59 (q, J=285.7, Hz, $CF_3$), 179.30 (q, J=33.9 Hz, CO).

Example 10d

Synthesis of bis(1,1,1,5,5,5-hexafluoro-2,4-pentanedionato)(N,N-diethylethylenediamine)zinc, $Zn(hfa)_2(N,N-DEA)$ (4)

This compound was synthesized and purified via an approach similar to that for 1, starting with 1.00 g (3.36 mmol) $Zn(NO_3)_2 \cdot 6H_2O$, 1.40 g (6.72 mmol) Hhfa, 0.40 g (6.72 mmol) 1-propylamine, and 0.39 g (3.36 mmol) N,N-diethylethylenediamine.

Yield: 1.13 g (56.4%). mp: 136-139° C. Anal. Calcd. for $C_{16}H_{18}O_4N_2F_{12}Zn$: C, 32.26; H, 3.05; N, 4.70. Found: C, 32.03; H, 2.92; N, 4.58. $^1$H NMR ($C_6D_6$, δ): 0.608 (t, 6H, $CH_3$), 0.88 (br s, 2H, $NH_2$), 1.67 (br s, 4H, $CH_2CH_3$), 2.044 (br s, 2H, $NCH_2CH_2NH_2$), 2.65 (br s, 2H, $NCH_2CH_2NH_2$), 6.25 (s, 2H, COCHCO). $^{13}$C NMR ($C_6D_6$, δ): 7.07 ($CH_3$), 35.34 (CH$_3$CH$_2$), 44.90 (CH$_3$C$_{H2}$NCH$_2$CH$_2$N), 53.94 (CH$_2$NH$_2$), 88.59 (CH), 117.60 (q, J=286.6, Hz, CF$_3$), 178.21 (q, J=33.8 Hz, CO).

Example 11

Characterization of Zinc Precursors

A. Molecular Structural Characteristics of Zinc Precursors

Single crystals of compounds 1, 3, and 4 were obtained from hexane solution by slow cooling. Crystallographic data were collected on a CCD area detector diffractometer with graphite-monochromated molybdenum (Mo) K-alpha radiation. Reflections were collected with a Bruker SMART detector and processed with SAINT-NT software from Bruker. Data were corrected for Lorentz and polarization effects. The structures were solved by direct methods and expanded using Fourier techniques. All non-hydrogen atoms were refined anisotropically. Hydrogen atoms were introduced in idealized positions but not refined. All calculations were performed using the Bruker SHELXTL crystallographic software package. All disordered atoms were refined with group anisotropic displacement parameters. The effect on the key metrical parameters of interest is negligible. The structure plots were produced using the ORTEP program. Single crystal X-ray diffraction data and refinement details relating to the structure determinations for Zn complexes 1, 3 and 4 are summarized in Table S1 below.

Figure 6:
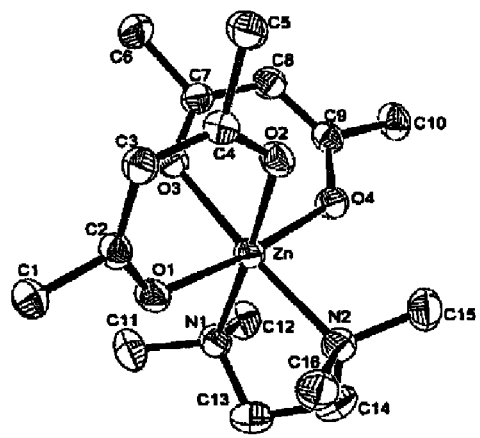
FIGS. 6A-6C are ORTEP drawings (50% ellipsoid probability) of the molecular structures of certain zinc MOCVD precursors according to the invention. Hydrogen and fluorine atoms have been omitted for clarity.
Figure 6:
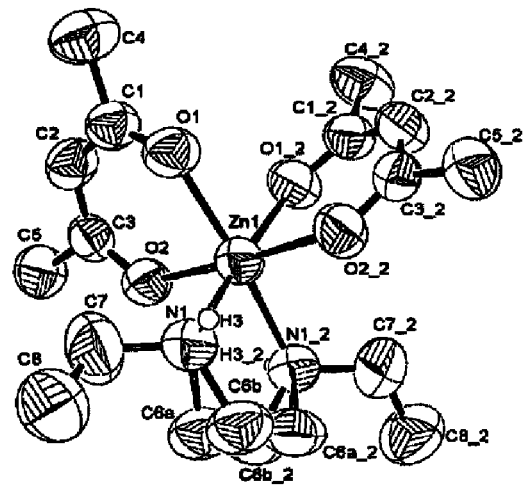
Figure 6:
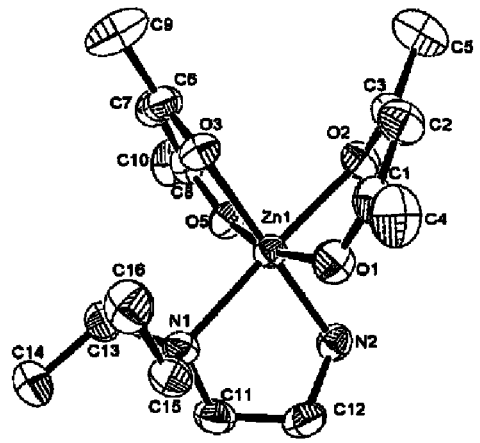

Single crystal X-ray diffraction experiments revealed that complexes 1, 3 and 4 were all monomeric (FIGS. 6A-C, respectively). Despite these complexes being synthesized via an aqueous route, coordinated water was not observed, and in all three complexes, the Zn$_{2+}$ ion appeared to be surrounded by β-diketonate and diamine ligands in a quasi-octahedral 6-coordinate geometry. N—Zn—N bond angles ranged from 84.60(16)° to 85.74(11)°, while trans ligand atom-Zn-ligand atom bond angles ranged from 166.68(10)° to 177.21(11)°, indicating distortion from an idealized octahedron. These structures stand in contrast to those of Zn(hfa)$_2$.2H$_2$O.polyether adducts in which the polyether does not bond directly to the Zn$^{2+}$ ion but instead interacts with coordinated water through hydrogen bonds. Without wishing to be bound to any particular theory, this difference may be attributed to the fact that a diamine is a stronger Lewis base and competes more favorably with water for the Zn$^{2+}$ ion than does the polyether.

The Zn—N bond lengths in complex 1 were 2.145(1) Å and 2.151(1) Å, and in complex 3 they were 2.125(3) Å. Without wishing to be bound to any particular theory, the shorter Zn—N bond lengths in complex 3 may be attributed to the difference in bulkiness between N,N,N',N'-tetraethylenediamine (TMEDA) and N,N'-dithylenediamine (N,N'-DEA) ligands. TMEDA, with four methyl groups on the two N atoms, may incur greater steric repulsion than does N,N'-DEA which has an ethyl group and a proton on each N atom.

TABLE S1

Crystallograhpic Data and Structure Refinement of Compounds 1, 3 and 4.

| | complex identity | | |
|---|---|---|---|
| | Zn(hfa)$_2$(TEMDA) 1 | Zn(hfa)$_2$(N,N'-DEA) 3 | Zn(hfa)$_2$(N,N-DEA) 4 |
| empirical formula | C$_{16}$H$_{13}$F$_{12}$N$_2$O$_4$Zn | C$_{16}$H$_{18}$F$_{12}$N$_2$O$_4$Zn | C$_{16}$H$_{18}$F$_{12}$N$_2$O$_4$Zn |
| formula weight | 595.69 | 595.69 | 595.69 |
| temperature (K) | 153(1) | 280(2) | 153(2) |
| wavelength (Å) | 0.71073 | 0.71073 | 0.71073 |
| crystal system | monoclinic | monoclinic | monoclinic |
| space group | P2$_1$/n | C2/c | P2$_1$/c |
| unit cell dimensions (Å) | | | |
| a | 13.2588(8) | 18.216(6) | 10.7229(11) |
| b | 10.3996(6) | 10.448(2) | 17.7077(19) |
| c | 17.3331(10) | 13.242(4) | 24.760(3) |
| unit cell angles (°) | | | |
| α | 90 | 90 | 90 |
| β | 108.54(1) | 105.61(2) | 90.91(1) |
| γ | 90 | 90 | 90 |
| volume (Å$^3$), Z | 2266.0(2), 4 | 2427.2(11), 4 | 4700.8(9), 8 |
| calc. density (g/cm$^3$) | 1.746 | 1.630 | 1.894 |
| abs coeff (mm$^{-1}$) | 1.208 | 1.128 | 1.310 |
| F(000) | 1192 | 1192 | 2682 |
| crystal size (mm) | 0.50 × 0.22 × 0.18 | 0.398 × 0.188 × 0.001 | 0.402 × 0.376 × 0.138 |
| θ range (°) | 1.70 to 28.96 | 2.27 to 28.97 | 1.41 to 29.00 |
| limiting indices | −17 ≤ h ≤ 17 −13 ≤ k ≤ 14 −23 ≤ l ≤ 22 | −24 ≤ h ≤ 23 −14 ≤ k ≤ 14 −18 ≤ l ≤ 17 | −13 ≤ h ≤ 13 −22 ≤ k ≤ 22 −31 ≤ l ≤ 31 |
| refl collected/unique | 20715/5549 | 11152/2977 | 43291/11275 |
| abs correction | none | integration | integration |
| max./min. trans. | | 0.9886/0.7544 | 0.8595/0.6333 |
| refinement method | full-matrix least-squares on F$^2$ | | |
| data/parameters | 5549/320 | 2977/192 | 11275/645 |
| GOF on F$^2$ | 1.037 | 0.953 | 1.024 |
| final R indices [I > 2σ(I)][a] | R$_1$ = 0.0277 wR$_2$ = 0.0723 | R$_1$ = 0.0447 wR$_2$ = 0.1222 | R$_1$ = 0.0562 wR$_2$ = 0.1513 |
| R indices (all data)[a] | R$_1$ = 0.0335 wR$_2$ = 0.0764 | R$_1$ = 0.0963 wR$_2$ = 0.1454 | R$_1$ = 0.0736 wR$_2$ = 0.1630 |
| largest diff. peak and hole (e−/Å$^{-3}$) | 0.396 and −0.285 | 0.307 and −0.255 | 1.018 and −0.682 |

[a]R$_1$ = Σ||F$_o$ − F$_c$||/Σ|F$_o$| and wR$_2$ = {Σ[w(F$_o^2$ − F$_c^2$)$^2$]/Σ[w(F$_o^2$)$^2$]}$^{1/2}$ The increased steric hindrance may result in slightly longer Zn—N bonds. This effect is demonstrated in the structure of complex 4. Due to the unsymmetrical nature of the N,N-diethylenediamine ligand in complex 4, the Zn—N (CH$_2$CH$_3$)$_2$ bond undergoes lengthening (average length 2.185(3) Å) while Zn—NH$_2$ shortens (average length 2.075 (3) Å). Variations in Zn—N bond lengths also can lead to variations in Zn—O bond lengths. In complex 4, the Zn—O bond trans to the elongated Zn—N bond averaged 2.181(2) Å, while the other five Zn—O bond lengths ranged from 2.083 (2) Å to 2.117(2) Å. The Zn—O distances in complexes 1 and 3 also fell into this range, which was longer than the 2.06 Å reported for hydrated Zn(hfa)$_2$, probably due to coordination of the ancillary diamine ligand. Selected bond lengths and angles are compiled in Table 4.

packing diagram of complex 4 reveals close intermolecular proximity of N and O atom pairs on different molecules, with neighboring molecules paired together along the c axis. The shortest intermolecular O—H$_2$N distance was 3.106 Å, and such short distances are indicative of relatively strong O—H—N hydrogen bonding. Thus, it is believed that at the molecular level, complex 4 is not a monomer, but crystallizes as a dimer bound via weak hydrogen bonds, which explains the high melting pointing and relatively low volatility of the solid. Although there exists an —NH(CH$_2$CH$_3$) group in complex 3, a similar proximity of N and O atoms was not observed, which may be due to the steric encumbrance introduced by the ethyl group attached to each N atom in complex 3. This steric screening may prevent any close approach of neighboring molecules.

TABLE 4

Selected bond lengths (Å) and bond angles (°) for complexes 1, 3, and 4.

| 1 | | 3 | | 4 | |
|---|---|---|---|---|---|
| Zn—O(1) | 2.103(1) | Zn(1)—O(1) | 2.111(2) | Zn(1)—O(1) | 2.102(2) |
| Zn—O(2) | 2.112(1) | Zn(1)—O(2) | 2.095(2) | Zn(1)—O(2) | 2.166(2) |
| Zn—O(3) | 2.126(1) | Zn(1)—N(1) | 2.125(3) | Zn(1)—O(3) | 2.083(2) |
| Zn—O(4) | 2.096(1) | | | Zn(1)—O(5) | 2.113(2) |
| Zn—N(2) | 2.145(1) | | | Zn(1)—N(1) | 2.194(3) |
| Zn—N(1) | 2.151(1) | | | Zn(1)—N(2) | 2.074(3) |
| O(4)—Zn—O(1) | 173.65(4) | O(2)—Zn(1)—O(2)_2 | 176.89(11) | N(2)—Zn(1)—O(3) | 177.21(11) |
| O(4)—Zn—O(2) | 90.98(4) | O(2)—Zn(1)—O(1)_2 | 91.69(8) | N(2)—Zn(1)—O(1) | 92.71(11) |
| O(1)—Zn—O(2) | 85.06(4) | O(2)_2—Zn(1)—O(1)_2 | 86.02(8) | O(3)—Zn(1)—O(1) | 89.91(10) |
| O(4)—Zn—O(3) | 85.09(4) | O(2)—Zn(1)—O(1) | 86.02(8) | N(2)—Zsn(1)—O(5) | 91.06(11) |
| O(1)—Zn—O(3) | 89.52(4) | O(2)_2—Zn(1)—O(1) | 91.69(8) | O(3)—Zn(1)—O(5) | 86.18(10) |
| O(2)—Zn—O(3) | 83.32(4) | O(1)_2—Zn(1)—O(1) | 85.15(12) | O(1)—Zn(1)—O(5) | 168.24(10) |
| O(4)—Zn—N(2) | 90.90(5) | O(2)—Zn(1)—N(1) | 94.52(10) | N(2)—Zn(1)—O(2) | 94.27(11) |
| O(1)—Zn—N(2) | 94.42(5) | O(2)_2—Zn(1)—N(1) | 87.79(10) | O(3)—Zn(1)—O(2) | 85.14(10) |
| O(2)—Zn—N(2) | 95.58(5) | O(1)_2—Zn(1)—N(1) | 173.79(10) | O(1)—Zn(1)—O(2) | 82.34(10) |
| O(3)—Zn—N(2) | 175.82(5) | O(1)—Zn(1)—N(1) | 95.46(11) | O(5)—Zn(1)—O(2) | 86.28(10) |
| O(4)—Zn—N(1) | 94.00(5) | O(2)—Zn(1)—N(1)_2 | 87.79(10) | O(3)—Zn(1)—N(1) | 95.92(10) |
| O(1)—Zn—N(1) | 89.85(5) | O(2)_2—Zn(1)—N(1)_2 | 94.52(10) | O(1)—Zn(1)—N(1) | 93.31(11) |
| O(2)—Zn—N(1) | 174.83(4) | O(1)_2—Zn(1)—N(1)_2 | 95.46(10) | O(5)—Zn(1)—N(1) | 98.12(11) |
| O(3)—Zn—N(1) | 95.71(5) | O(1)—Zn(1)—N(1)_2 | 173.79(10) | O(2)—Zn(1)—N(1) | 175.52(10) |
| N(2)—Zn—N(1) | 85.74(5) | N(1)—Zn(1)—N(1)_2 | 84.60(16) | N(2)—Zn(1)—N(1) | 84.88(11) |

It is also interesting to compare the metrical parameters of complex 1, Zn(hfa)2(TMEDA), to the structurally similar complex Zn(dpm)$_2$(TMEDA), where methyl groups replace the F atoms on the diketonate skeleton. In Zn(dpm)$_2$ (TMEDA), the average Zn—N bond length was 2.245(3) Å, longer than the average Zn—N bond length found in complex 1, 2.148(1) Å, while the average Zn—O bond length was 2.044(2) Å, shorter than the average Zn—O bond length in 1 [2.109(1) Å]. Without wishing to be bound to any particular theory, it is believed that this variation in Zn-ligand contacts suggests that the electron-withdrawing characteristics of the hfa ligand increase the Lewis acidity of Zn$^{2+}$ and in turn strengthen the bonding between the Zn$^{2+}$ center and the neutral ancillary ligands. The melting point of Zn(dpm)$_2$ (TMEDA) is reported to be 196-202° C., about 90° C. higher than that of 1, 106-108° C. The significantly lower melting point of 1 can be attributed to, among other factors, the reduced intermolecular interactions in the fluorocarbon-substituted complex.

Figure 7:
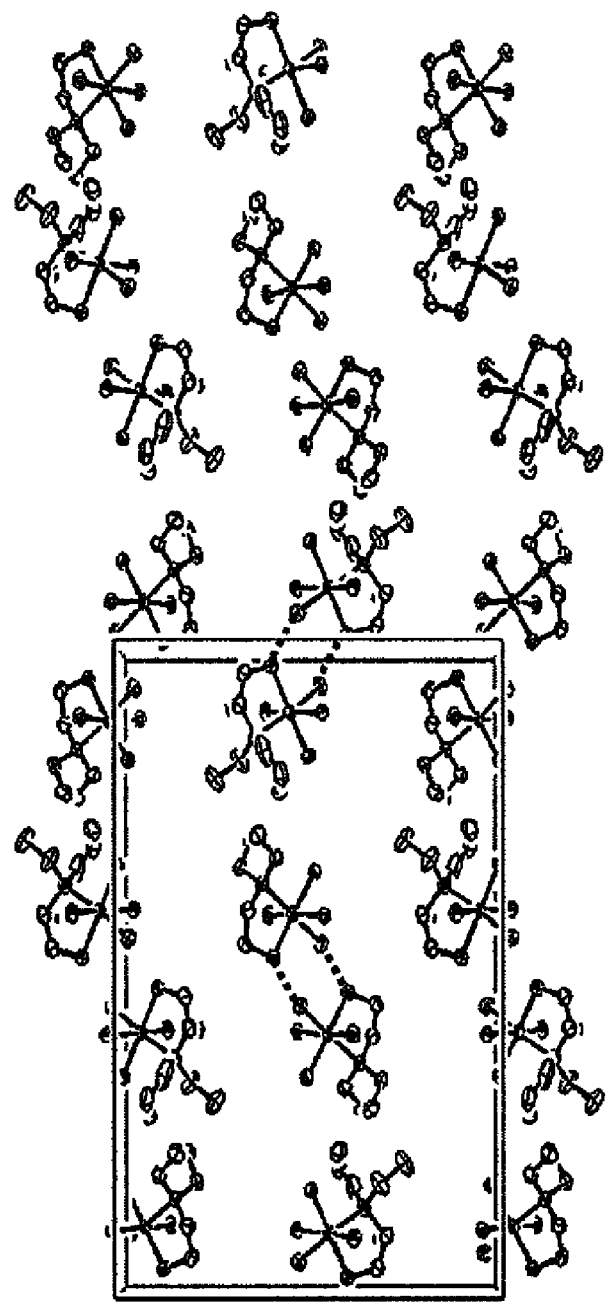
FIG. 7 is a packing diagram of the precursor of FIG. 6C viewed along the c axis. Carbon atoms on diketonate ligands, fluorine and hydrogen atoms have been omitted for clarity. Dotted lines connect the nearest hydrogen bonded O and NH2 groups. The distance is 3.106 Å.
Figure 8A:
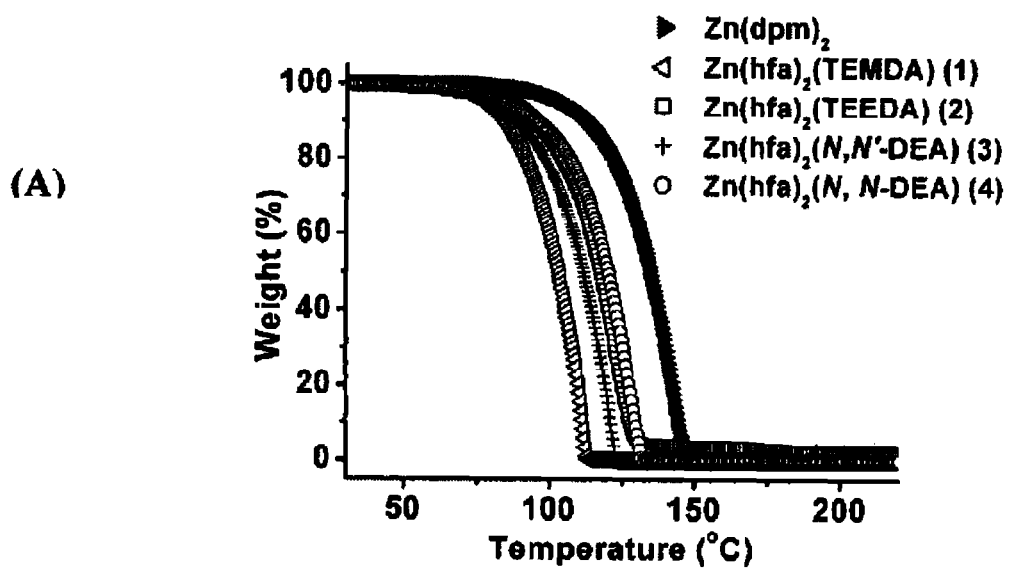
FIG. 8A is a low-pressure TGA comparison of the volatilities of certain zinc MOCVD precursors of the invention and Zn(dpm)2.
Figure 8B:
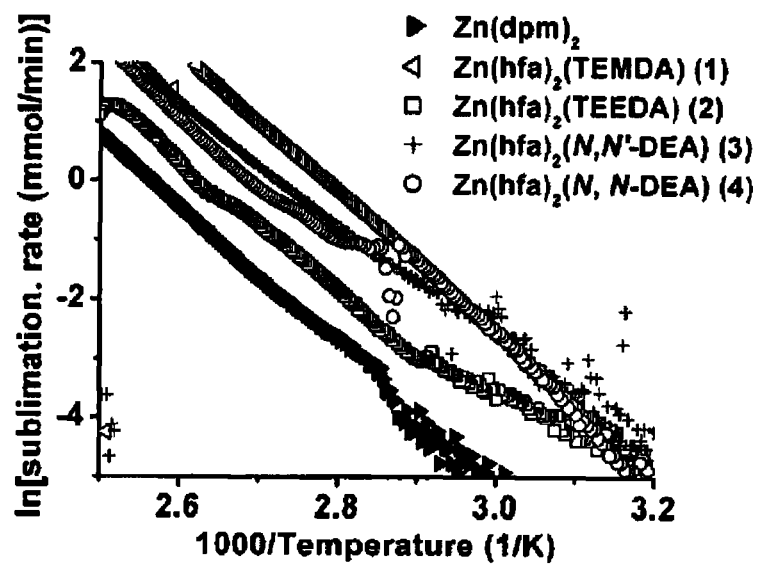
FIG. 8B is a thermal activation volatility comparison of certain zinc MOCVD precursors and Zn(dpm)2.

Complex 4 had an unexpectedly high melting point and lower than average volatility (see below) than the other three complexes. Examination of a packing diagram (FIG. 7) shows that these properties are likely due to extensive intermolecular hydrogen bonding. However, since protons bonded to the N atoms in complex 4 were not specifically located in the Fourier map, it is not possible to present a completely quantitative description of the hydrogen bonding metrical parameters. Nevertheless, careful examination of the B. Volatility Characteristics of Zinc Precursors Reduced pressure thermogravimetric analysis (TGA) was performed on complexes 1-4 to investigate their volatility characteristics. FIG. 8A compares weight loss properties of these complexes with the conventional Zn MOCVD precursor, Zn(dpm)$_2$. Although complex 2 appeared to sublime with about 3% residue, which may be attributed to decomposition at elevated temperatures, all four complexes exhibited increased volatility compared to Zn(dpm)$_2$. The smoothness of the curves also may indicate that the coordinated diamine does not dissociate during heating. FIG. 8B presents thermal activation plots of the sublimation rates. All four Zn(hfa)$_2$. diamine complexes had higher vaporization rates/lower vaporization activation energies than Zn(dpm)$_2$ under typical MOCVD reactor conditions.

Example 12

Preparation of indium MOCVD precursor. Synthesis of tris(2,2,6,6-tetramethyl-3,5-heptanedionato)indium, In(dpm)$_3$.

This compound was synthesized following the procedure described in Jablonski et al. (1979), *Spectrochim. Acta, Part A*, 35: 1297 and Utsunomi (1971), *Bull. Chem. Soc. Jpn.*, 44: 2688.

mp: 169-172° C. Anal. Calcd. for C$_{33}$H$_{57}$O$_6$In: C, 59.64; H, 8.64. Found: C, 59.25; H, 8.76. $^1$H NMR (C$_6$D$_6$, δ): 1.19 (s, 54H, CH$_3$), 5.84 (s, 3H, COCHCO).

Example 13

Preparation of tin MOCVD precursor. Synthesis of bis(2, 4-pentanedionato)tin(II), $Sn(acac)_2$.

This compound was synthesized following the procedure described in Ewings et al. (1975), *J. Chem. Soc.*, Dalton Trans., 821 and Bos et al. (1973), *Inorg. Nucl. Chem. Lett.*, 9:961.

bp: 94-96° C./0.04 Torr. Anal. Calcd. for $C_{10}H_{14}O_4In$: C, 37.90; H, 4.45. Found: C, 38.37; H, 4.59. $^1H$ NMR ($CDCl_3$, δ): 1.65 (s, 12H, $CH_3$), 5.07 (s, 2H, COCHCO).

Example 14

Preparation of ZITO thin films by MOCVD. Zn—In—Sn oxide (ZITO) thin films were grown in a horizontal hot-wall MOCVD reactor (FIG. 4) similar to the one described in Ni et al. (2005), J. Am. Chem. Soc., 127: 5613-5624 and Hinds et al. (1997), J. Mater. Res., 12(5): 1214-1236, the disclosures of which are incorporated by reference herein in their entirety. Specifically, metal-organic precursor reservoirs were individually heated by thermostated oil baths, and argon carrier flows were mixed in a common manifold. Precursors were maintained in vacuo or under atmospheric pressure of argon while being heated, to prevent reaction with atmospheric moisture. For uniformity of deposition rate over large substrate areas, a quartz laminar flow chamber was utilized. The 3:1 aspect ratio of cross section width-to-height (6.0×2.0 cm) in this flow chamber reduced thermal buoyancy effects, thus enhancing the stability of the carrier flow. A silicon carbide-(SiC—) coated graphite susceptor was positioned at the end of the flow chamber and was angled at 8.7° to aid uniformity of deposition along the length of the substrate. The susceptor was heated by a 6 kW, water-cooled infrared (IR) lamp (Research Inc.), and temperature was monitored with a K-type thermocouple on the surface of the susceptor. Argon (Ar) and oxygen ($O_2$) carrier flows were regulated by Unit 1400A mass flow controllers. Water flow was controlled by the oxygen flow and a constant bleed valve setting, with water flow rates determined by weight loss. Pressure was controlled by a throttle valve and was measured by an MKS 122AA capacitance manometer.

Four series of ZITO thin films were prepared. Within each series the Zn:In ratio was held constant while the Sn:Zn ratio was varied. The Zn:In ratio was then varied between series. The compositions of the individual films are listed in Table S11 below. Because among the four complexes from Example 1, complex 3 had the lowest melting point, it was used to grow samples of the ZITO thin films of the invention. Under typical growth conditions, complex 3 should be a liquid in the thermostated MOCVD reactor precursor reservoir. Being a liquid under these conditions affords substantially constant surface area and vaporization rate, which were found to improve compositional reproducibility in film growth. Using $Zn(hfa)_2(N,N'-DEA)$ (3), $In(dpm)_3$, and $Sn(acac)_2$ as precursors, films with the nominal composition $ZnIn_xSn_yO_z$ (1.5<x<4.0, 0.5<y<2.5) were grown on Corning 1737F glass substrates at 500° C. The Corning 1737F glass substrates were sonicated first in hexane, then in acetone for 10 minutes before deposition. The precursor reservoirs containing $Zn(hfa)_2(N,N'-DEA)$ (complex 3), $In(dpm)3$, and $Sn(acac)2$ were maintained at what was found by experimentation to be preferred temperatures of: 68° C., 105° C., and room temperature, respectively.

The composition of the ZITO films was controlled by varying the Ar carrier gas flow rates. The carrier gas was mixed with $O_2$ immediately upstream of the susceptor in the reactor, with an $O_2$ flow rate varying from 100-120 sccm. A preferred susceptor temperature was determined, after some experimentation, to be about 500° C. with an operating system pressure of ca. 3 Torr throughout film growth process. The film growth rate was estimated to be about 3 nm/min under these conditions.

Example 15

Characterization of ZITO thin films. X-ray θ-2θ scans (XRD) of the MOCVD-derived ZITO films were performed on a Rigaku DMAX-A powder diffractometer using nickel-(Ni)-filtered copper (Cu) Kα radiation calibrated with silicon (Si) sprinkled on the film surface. Transmission electron microscopic (TEM) images were obtained on a Hitachi 8100 microscope operating at 200 KeV. Optical transmission data were recorded on a Cary 500 UV-Vis-NIR spectrometer from 300 nm to 3300 nm with an uncoated Corning 1737F glass substrate as reference. Film compositions were assayed using inductively coupled plasma atomic emission spectroscopy (ICP-AES) on an Atomscan 25 spectrometer after films were dissolved in hydrochloric acid. Film thickness was investigated with a Tencor P10 surface profiler after etching a step in the film with hydrochloric acid. The surface morphology of the ZITO films was investigated on a Digital Instruments Nanoscope III atomic force microscope (AFM) operating in the contact mode. Room temperature four-probe charge transport data were acquired on a Bio-Rad HL5500 Hall effect measurement system at ambient temperature. Variable-temperature charge transport measurements were recorded between 77 K and 330 K using instrumentation described previously. X-ray photoelectron spectroscopy (XPS) of films was performed on an Omicron ESCAPROBE system using aluminum (Al) Kα radiation.

A. Microstructural Properties of ZITO Films

Figure 9:
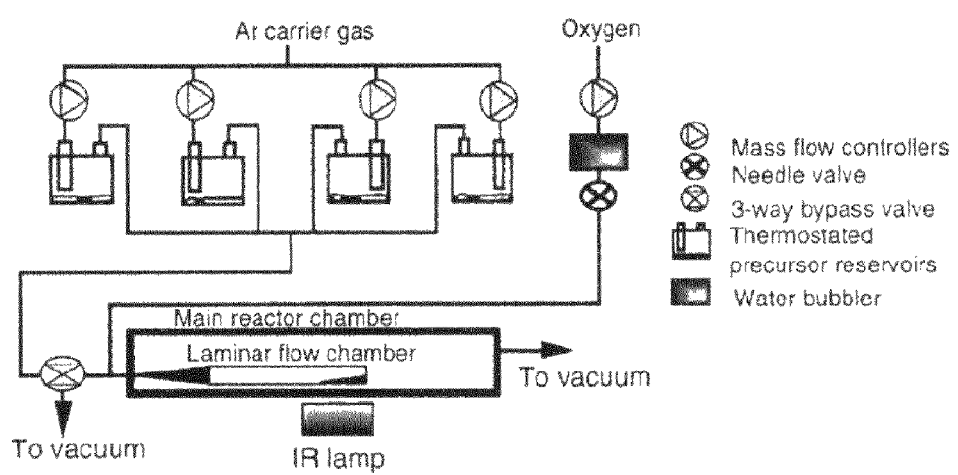
FIG. 9 is a schematic diagram of a horizontal hot-wall MOCVD reactor.

Each of the thin films prepared exhibited a polycrystalline microstructure as evidenced by XRD and electron diffraction patterns. The plan-view TEM image of a structurally/electrically representative film revealed discrete grains with sizes ranging from 100 nm to 200 nm (FIG. 9A), in good agreement with AFM and SEM data. The electron diffraction pattern was consistent with a randomly oriented $In_2O_3$ crystal structure (FIG. 9B). Deposited films were quite smooth by AFM, with root-mean-square (RMS) roughnesses no greater than 2% of the film thickness.

In bulk ZITO materials, it is generally known that a minimum In content of 60 cation % is required to retain the $In_2O_3$ bixbyite structure for Zn- and Sn-cosubstituted $In_2O_3$. However, it is also possible to overdope a slight amount of Zn into the material without forming new phases. The present teachings reveal that the solubility of ZnO and $SnO_2$ in $In_2O_3$ is greater in MOCVD-derived thin films. Given that the experimentally used deposition conditions for these thin films (e.g., about 500° C. and about 3 Torr working pressure) were unlike the thermodynamic equilibrium regime where ZITO bulk materials are typically synthesized (e.g., about 1100° C. to about 1250° C. and about 1 atm), the MOCVD-derived ZITO thin films were believed to be composed of a metastable phase, a common observation in thin film synthesis by MOCVD.

Figure 10:
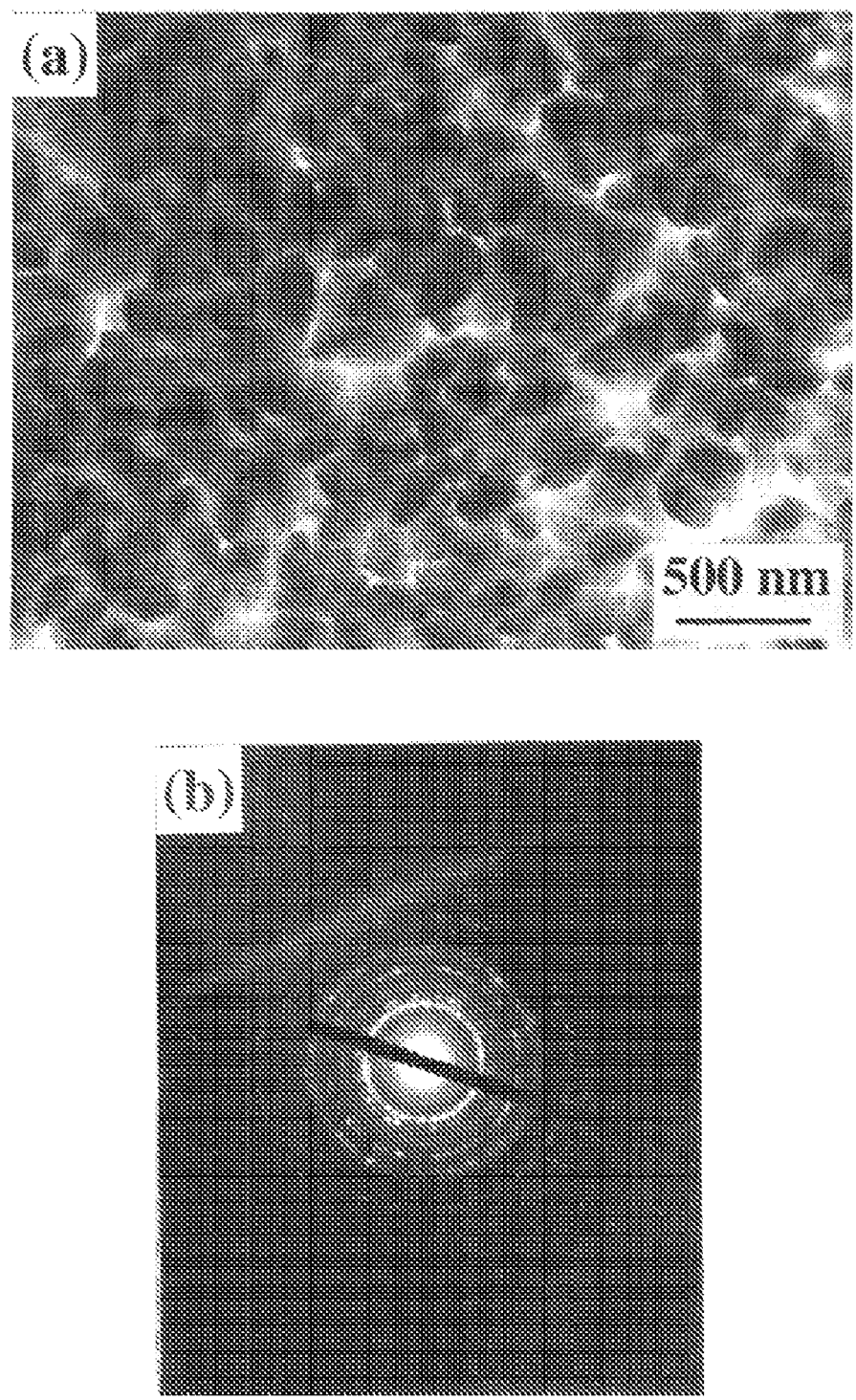
FIG. 10A is a plan-view TEM image of a ZITO thin film of the invention.
FIG. 10B is a corresponding electron diffraction pattern showing the $In_2O_3$ crystal structure.

It was found by XRD (FIGS. 10A and 10B) that at high In content, the MOCVD-derived ZITO films can be indexed in the $In_2O_3$ bixbyite structure (JCPDS Card No. 06-416). The predominant (222) and (400) reflections indicated some degree of texturing of the films on the glass substrate. As the In content was decreased, the reflections broaden, and finally, when Zn and Sn reached the solubility limit at about x=1.7 and y=1.0, the characteristic reflections of the ZnO and/or SnO2 phases appeared in the XRD patterns. The lowest In content tested for which the films retain a phase-pure bixbyite structure was found to be a remarkable about 40 cation %, while in commercial ITO thin films the In content typically is near 90 cation %. The present results are in qualitative agreement with the bulk phase findings of Poeppelmeier et al. in Palmer et al. (1997), Chem. Mater., 9: 3121, that cosubstitution of Zn with Sn in $In_2O_3$ dramatically increases the solubility of both $SnO_2$ and ZnO. In accordance with the present teachings, it is believed that the In content can be reduced even lower while maintaining the advantageous properties in the final thin film.

Use of fluorinated MOCVD precursors raises the possibility that the deposited films may contain $F^-$, either as a dopant or as a discrete fluoride-containing phase. Water is a commonly used co-reactant during MOCVD growth with fluorinated precursors to reduce unnecessary fluorine-containing products in MOCVD processes. For the ZITO films discussed herein, water was not used because the Sn precursor, $Sn(acac)_2$, is moisture-sensitive and undergoes rapid reaction with water before reaching the film growth area. Even without water, the deposited films exhibited no detectable fluoride phases in the XRD patterns. All films were also subjected to in-depth XPS analysis with sputter-cleaning of the surfaces. The fluoride content was found to be below the detection limits of the XPS instrumentation (<0.2 atomic %).

B. Charge Transport Properties of ZITO Thin Films

In the following discussion, trace fluoride influence on charge transport properties of the films was not considered. Note however that if there is fluoride contamination, it should be beneficial to the properties of the films since it would be expected to increase the carrier concentration and thus the conductivity.

Figure 11A:
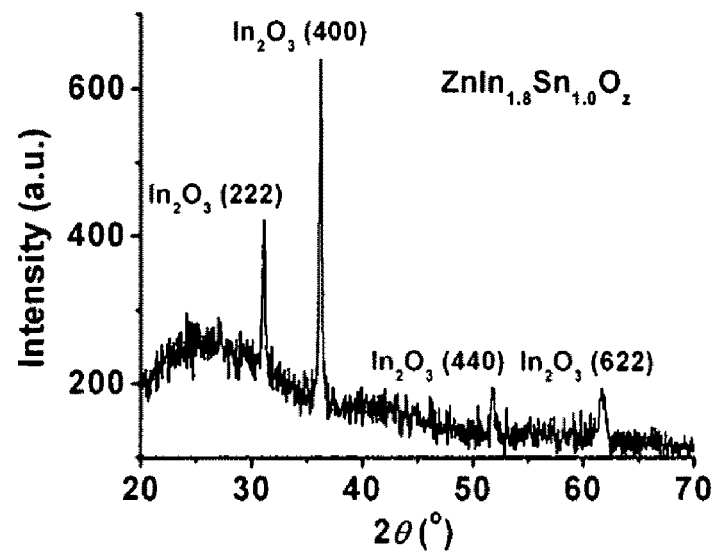
FIG. 11A is a θ-2θ X-ray diffraction scan of an embodiment of a ZITO thin film of the invention, showing the predominant $In_2O_3$ crystal structure. The broad peak between 22° and 28° is due to glass substrate.
Figure 11B:
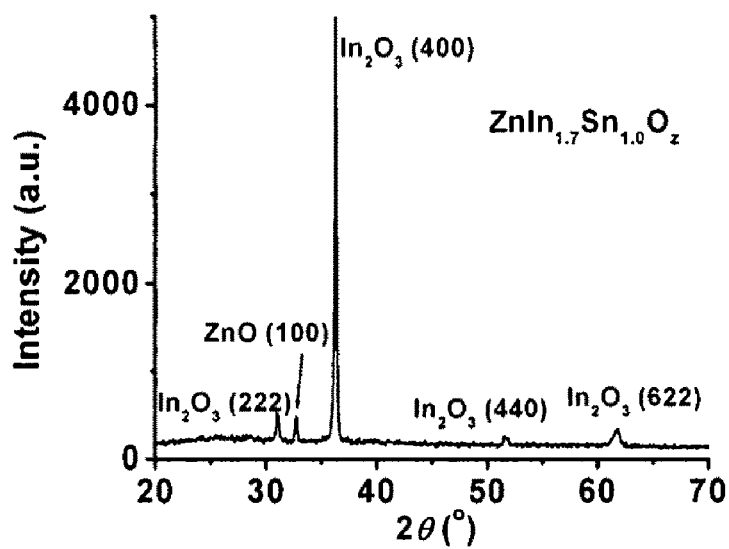
FIG. 11B is a θ-2θ X-ray diffraction scan of another embodiment of the ZITO thin film of the invention, showing both doped $In_2O_3$ and ZnO phases.

Room temperature charge transport data suggested that the electrical properties of the MOCVD-derived ZITO films are closely related to their chemical compositions. These data are summarized in Table S11 below and graphically represented in FIG. 11.

TABLE S11

Room temperature electrical and optical properties of as-grown ZITO films on Corning 1737F glass substrate.

| Composition | Conductivity (S/cm) | Mobility ($cm^2/Vs$) | Carrier Concentration ($10^{20} cm^{-3}$) | Bandgap (eV) |
|---|---|---|---|---|
| $ZnIn_{1.8}Sn_{0.55}O_z$ | 793 | 34.2 | 1.45 | 3.71 |
| $ZnIn_{1.8}Sn_{0.97}O_z$ | 1013 | 32.0 | 1.98 | 3.80 |
| $ZnIn_{1.8}Sn_{1.33}O_z$ | 1605 | 35.2 | 2.85 | 3.90 |
| $ZnIn_{1.8}Sn_{1.56}O_z$ | 1668 | 35.0 | 3.01 | 2.87 |
| $ZnIn_{1.8}Sn_{1.65}O_z$ | 1652 | 33.2 | 3.11 | 2.87 |
| $ZnIn_{1.8}Sn_{1.74}O_z$ | 1450 | 28.8 | 3.15 | 2.90 |
| $ZnIn_{2.0}Sn_{0.85}O_z$ | 1002 | 35.8 | 1.75 | 3.73 |
| $ZnIn_{2.0}Sn_{1.05}O_z$ | 1290 | 38.2 | 2.12 | 3.77 |
| $ZnIn_{2.0}Sn_{1.16}O_z$ | 1644 | 34.8 | 2.95 | 3.84 |
| $ZnIn_{2.0}Sn_{1.50}O_z$ | 2150 | 37.4 | 3.56 | 3.88 |
| $ZnIn_{2.0}Sn_{1.68}O_z$ | 1860 | 34.2 | 3.41 | 3.90 |
| $ZnIn_{2.0}Sn_{1.79}O_z$ | 1530 | 29.0 | 3.30 | 3.90 |
| $ZnIn_{2.5}Sn_{0.67}O_z$ | 1090 | 38.2 | 1.43 | 3.72 |
| $ZnIn_{2.5}Sn_{0.97}O_z$ | 1113 | 38.0 | 1.81 | 3.73 |
| $ZnIn_{2.5}Sn_{1.36}O_z$ | 1240 | 38.8 | 2.00 | 3.72 |
| $ZnIn_{2.5}Sn_{1.50}O_z$ | 1274 | 35.7 | 2.23 | 3.80 |
| $ZnIn_{2.5}Sn_{1.66}O_z$ | 1550 | 36.6 | 2.65 | 3.83 |
| $ZnIn_{2.5}Sn_{1.83}O_z$ | 1357 | 34.2 | 2.48 | 3.80 |
| $ZnIn_{3.0}Sn_{0.53}O_z$ | 740 | 37.2 | 1.24 | 3.65 |
| $ZnIn_{3.0}Sn_{0.98}O_z$ | 847 | 36.5 | 1.45 | 3.72 |
| $ZnIn_{3.0}Sn_{1.51}O_z$ | 1114 | 35.9 | 1.94 | 3.75 |
| $ZnIn_{3.0}Sn_{1.61}O_z$ | 1400 | 36.6 | 2.39 | 3.80 |
| $ZnIn_{3.0}Sn_{1.76}O_z$ | 1359 | 36.0 | 2.36 | 3.80 |
| $ZnIn_{3.0}Sn_{1.85}O_z$ | 1330 | 35.8 | 2.32 | 3.79 |

As shown, conductivities first increase with addition of Sn, then decrease after reaching a maximum value. The film having the highest conductivity was found to have a nominal composition of $ZnIn_{2.0}Sn_{1.5}O_z$, with a conductivity of 2150 S/cm. All films are n-type, meaning that the majority carriers are electrons. Tin doping leads to an increase in carrier concentration until the carrier concentration reaches a maximum and beyond that point, the carrier concentration either leveled off or decreased slightly. While Sn doping generally increased the carrier concentration in these ZITO films, it tends to have a negative overall impact on carrier mobility. In fact, both Zn and Sn doping led to decrease in carrier mobility.

Figure 12:
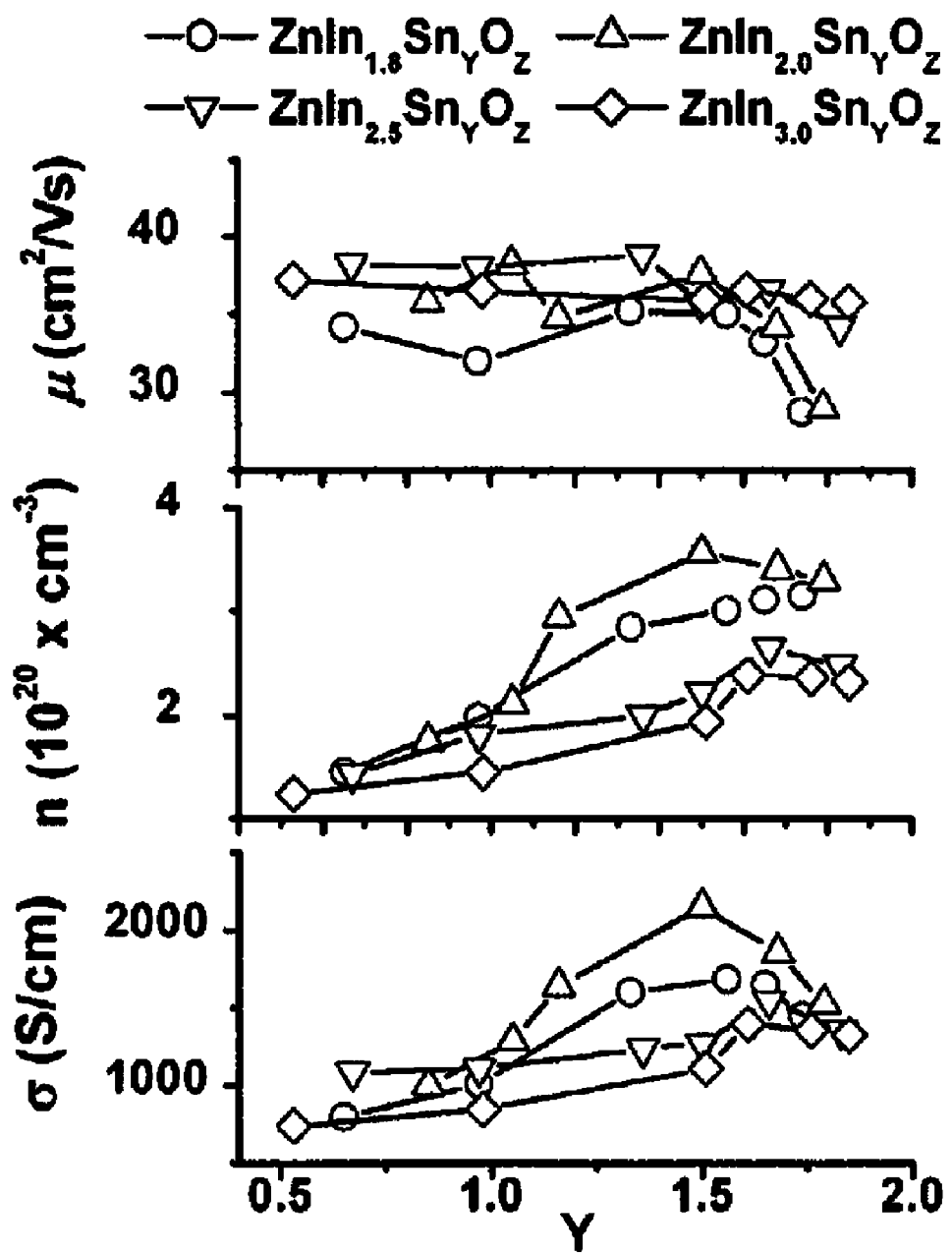
FIG. 12 is a room temperature conductivity-composition, carrier concentration-composition, carrier mobility-composition plots of certain embodiments of a ZITO thin film of the invention, wherein σ is conductivity, n is carrier concentration, and μ is carrier mobility. Lines through the data points are drawn as a guide to the eye.

Variable-temperature charge transport data for a representative ZITO film are shown in FIG. 12. Both conductivity and carrier mobility decreased slightly as temperature increased from 78 K to 330 K, revealing a modest "metal-like" charge transport behavior ($d\sigma/dt<0$), while carrier concentration remained substantially constant. Carrier mobility was found to scale approximately as $T^{-0.26}$.

In ITO, carriers can be generated in two ways: a) by oxygen vacancies; b) by Sn doping. Without wishing to be bound to any particular theory, it is believed that each oxygen vacancy contributes two electrons while each $Sn^{4+}$ replacement for $In^{3+}$ contributes one electron. Note however that Sn doping efficiency is known to be low, and much of the Sn is postulated to form neutrally charged species which do not contribute free electrons. Since in ZITO there is Zn as well as Sn doping, where each $Zn^{2+}$ theoretically contributes one hole, the carrier concentration in ZITO can be formally expressed as $[Sn_{In}^{\bullet}]-[Zn_{In}']+2n$, where $[Sn_{In}^{\bullet}]$ and $[Zn_{In}']$ are the concentrations of Sn and Zn that are electrically-active, while n is the concentration of oxygen vacancies. Note that in the ZITO films investigated here, even at high Zn content ([Sn]<[Zn]), the majority carriers in all four ZITO series are still electrons. Any holes generated by Zn addition are apparently insufficient to offset electrons arising from Sn doping and oxygen vacancies. It has been proposed that not all Zn cations contribute holes, but rather some form neutral associates with oxygen vacancies such as $(2 Zn_{In}'V_O^{\bullet\bullet})^x$, thus reducing the Zn doping efficiency. The result is $[Zn_{In}']<[Sn_{In}^{\bullet}]+2n$ and the majority carriers are still electrons. This assertion is in good agreement with the findings in bulk ZITO materials and other p-doped $In_2O_3$ TCOs. Thus, an increase in Sn content does not always lead to increases in carrier concentrations as evident in FIG. 11. At very high Sn contents, it is more likely for two Sn atoms to find neighboring sites and form neutral non-reducible $(Sn_2O_4)^x$ species. Under the film growth conditions discussed herein, there should also be a significant quantity of Sn species forming another neutral oxide complex that fills empty anion sites in the $In_2O_3$ matrix: $(2Sn_{In}^{\bullet}O_i'')^x$. The existence of $(2Sn_{In}^{\bullet}O_i'')^x$ is also supported by the annealing study where heating ZITO films in vacuum increases carrier concentration due to the release of $O_2$ from $(2Sn_{In}^{\bullet}O_i'')^x$ Scheme 2). Therefore, beyond a critical point, introducing additional Sn does not appear to increase the carrier concentration. Despite the high Sn doping level in the present ZITO system (Sn content ranging from 11-38 cation %) compared to that in typical ITO, the highest carrier concentration achieved in as-grown films was $3.56\times10^{20}$ $cm^{-3}$, lower than the $8-10\times10^{20}$ $cm^{-3}$ value typically found in polycrystalline ITO films. Without wishing to be bound to any particular theory, it is believed that this is the result of both Zn doping and neutral species formation. While Zn doping neutralizes free electrons, formation of neutral species reduces the Sn doping efficiency.

Scheme 2.
Dissociation of $(2Sn_{In}\cdot O_i'')^x$ and release of free carriers upon annealing.

$(2Sn_{In}\cdot O_i'')^x \longrightarrow \tfrac{1}{2}O_2(g) + 2Sn\bullet + 2e'$

In principle, carrier mobility is determined by a variety of carrier scattering mechanisms. Ionized impurity scattering (IIS) and lattice vibration scattering (LVS) are thought to be the more important scattering mechanisms in typical TCO materials. Grain boundary scattering (GBS) tends to be only important in polycrystalline films having very small grain sizes. The effect of neutral impurity scattering (NIS) on carrier mobility in TCOs is still a subject of debate. The average grain size of the present ZITO films is estimated to be greater than about 100 nm from the electron microscopy and AFM images (see above), which is larger than the estimated electron-mean-free path in typical TCO films, where it is about 10 nm. For these reasons, it is believed that in the MOCVD-derived ZITO films discussed herein, GBS plays a minor role in carrier mobility. Because mobility scales only weakly with temperature ($\mu \propto T^{-0.26}$, FIG. 12), it is thought that temperature-independent scattering mechanisms (IIS and/or NIS) influence carrier mobility as do temperature-dependent LVS mechanisms. The data show that doping of Zn and Sn generally has a negative effect on carrier mobility in ZITO films, e.g., higher doping levels lead to significantly lower carrier mobilities. This trend is in agreement with established models arguing that $Zn^{2+}$ and $Sn^{4+}$ can both act as ionized centers and scatter carriers. Note also that at high Sn concentrations, where increases in Sn content have either negligible or negative effects on carrier concentration, mobilities also tend to be depressed. If IIS and LVS were the exclusive scattering mechanisms that influence carrier mobility, then mobility should not decline greatly after carrier concentration peaks since the density of ionized defects remains stable. The observation that carrier mobility continuing to decrease with increased Sn content suggests that another scattering mechanism may have a significant influence on carrier mobility. When further Sn doping no longer increases carrier concentration, the additional Sn atoms should no longer act as ionized centers, but instead act as neutral species. In the present teachings, increasing the quantity of Sn added to the $In_2O_3$ matrix should form increasing quantities of neutral species. Thus, it is believed that at high Sn doping levels, in addition to IIS and LVS, NIS is also an important factor in determining carrier mobility.

C. Optical Properties of ZITO Thin Films

Regarding optical properties, the present MOCVD-derived ZITO films were transparent, e.g., all films exhibiting 80% or greater transmittance between 400 nm and 1500 nm. The absorption coefficients of the ZITO films indicated that the transparency of these films is comparable to or greater than that of commercial ITO. The UV-Vis-NIR spectrum of a representative ZITO film is presented in FIG. 13.

Note that ZITO films were more transparent at shorter wavelengths and that the ZITO plasmon edge in the NIR, which is due to free carrier absorption/reflection, exhibited a significant red shift versus ITO. Band gaps of the films, estimated from plotting $(ahv)^2$ against photon energy assuming a direct bandgap, vary from 3.65 eV to 3.90 eV (Table S11), falling within the 3.6-4.2 eV range reported for ITO.

Figure 13:
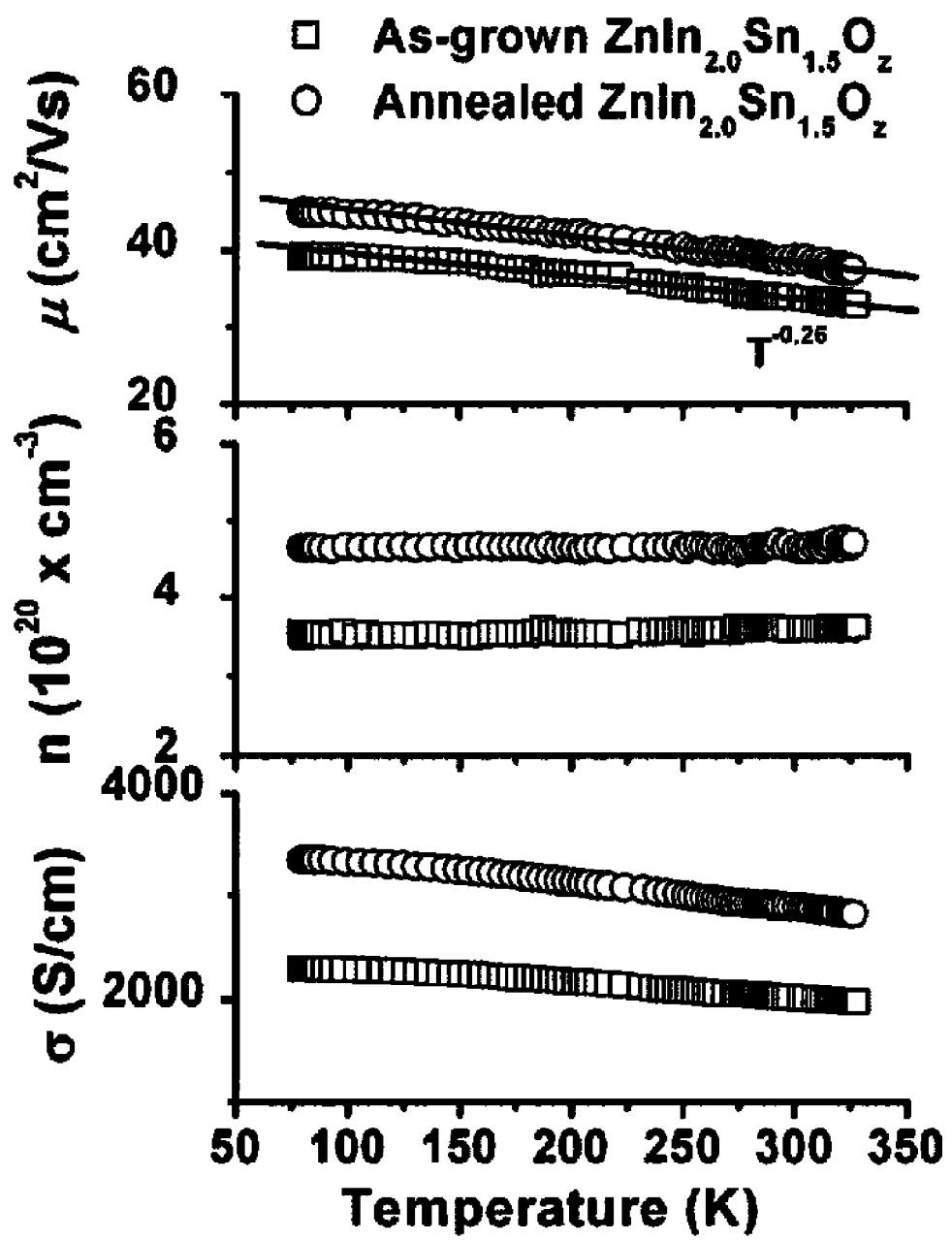
FIG. 13 is a variable-temperature charge transport measurements on an exemplary ZITO thin film of the invention before and after annealing in vacuum at 500° C. for 1.5 hr. σ: conductivity; n: carrier concentration; μ: carrier mobility.

With continued reference to FIG. 13, the increase in optical bandgap with increasing carrier concentration in ZITO films can be attributed to a band filling-dependent Burstein-Moss shift. The superior transparency of ZITO films in the near-IR range compared to that of ITO can then be ascribed to the relatively low carrier concentrations of the ZITO films.

D. Chemical Reactivity of ZITO Thin Films

All of the MOCVD-derived ZITO films exhibited appreciable chemical inertness. It typically requires more than 1 hour to dissolve a 200 nm thick ZITO film in concentrated hydrochloric acid, while less than 15 min. is required for a commercial 130 nm thick ITO film. Poly(3,4-ethylenedioxythiophene)-polystyrenesulfonate (PEDOT-PSS) is commonly used in PLED/OLED devices to improve hole injection and device performance. It is well-established that since PEDOT-PSS is highly acidic (pH~1), it etches the anode (ITO) layer, a process that destabilizes the ITO/PEDOT-PSS interface and compromises charge injection. Experiments were conducted to show that ZITO is significantly more resistant to PEDOT-PSS attack than ITO as assessed by the quantity of free In found in the PEDOT-PSS layer by XPS.

Figure 14A:
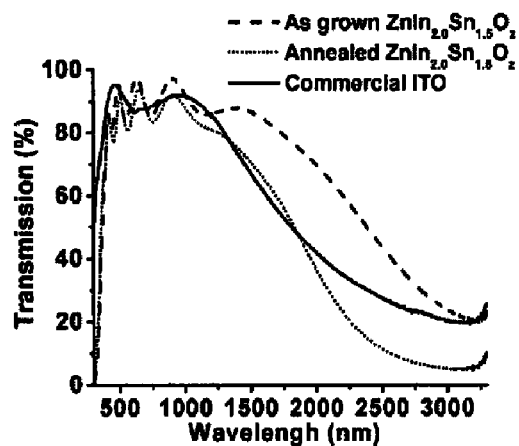
FIG. 14A is a UV-Vis-NIR spectra of an as-grown ZITO thin film of the invention, the same film after annealing, and a commercial ITO film. The ZITO film thickness is 340 nm, while the ITO film thickness is 130 nm.
Figure 14B:
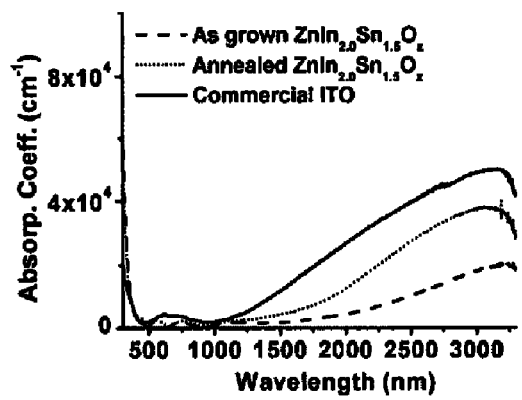
FIG. 14B is a corresponding absorption coefficients as a function of wavelength plot.
Figure 14C:
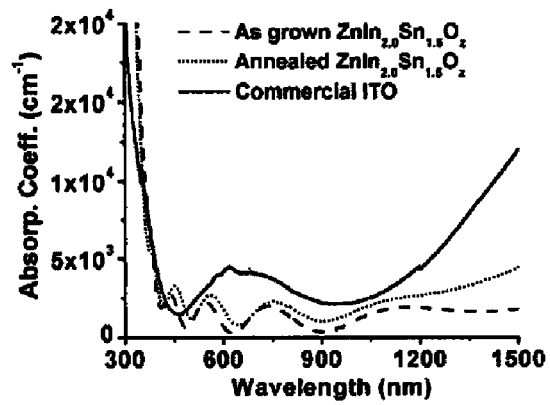
FIG. 14C is an enlargement of FIG. 14B from 300 nm to 1500 nm.

A 50 nm layer of PEDOT-PSS was spin-cast on both a cleaned commercial ITO film and an MOCVD-derived $ZnIn_{2.0}Sn_{1.5}O_z$ film cleaned by same procedure. The two samples were subsequently placed into a vacuum oven at 200° C. for 1 hour (common PEDOT-PSS curing conditions). Subsequent XPS measurements reveal that the In content at the surface of the PEDOT-PSS layer was about 1.1 atomic % for the ITO-based sample and greater than about 0.05 atomic % for the $ZnIn_{2.0}Sn_{1.5}O_z$-based sample (FIG. 14). Considering that the In content of $ZnIn_{2.0}Sn_{1.5}O_z$ is approximately half of that in ITO, the PEDOT-PSS dissolves greater than ten times more ITO than it does $ZnIn_{2.0}Sn_{1.5}O_z$.

Example 16

Effect of Annealing on As-Grown ZITO films. Annealing of the as-grown ZITO films was performed in the same reactor at 500° C. for 1.5 hr. under vacuum (pressure less than about 0.01 Torr).

Annealing of the present ZITO films in vacuum (pressure less than about 0.01 Torr) at 500° C. generally has led to a 20-40% increase in conductivity. Charge transport and optical data for a $ZnIn_{2.0}Sn_{1.5}O_z$ film before and after annealing are shown in FIGS. 12, 13 and in Table 5. Annealing caused a slight increase in carrier mobility, but a more pronounced increase in carrier concentration. As a result, the conductivity of $ZnIn_{2.0}Sn_{1.5}O_z$ increased from 2150 S/cm to 2890 S/cm. The annealed films also had a widened bandgap and a blue shift of the plasmon edge compared to the as-grown films. The overall optical transmission of the annealed ZITO films decreased (FIG. 13).

TABLE 5

Comparison of room temperature charge transport and optical properties of a $ZnIn_{2.0}Sn_{1.5}O_z$ film before and after annealing.

| $ZnIn_{2.0}Sn_{1.5}O_z$ | $\sigma_{298}$ (S/cm) | $\mu_{298}$ (cm$^2$/Vs) | $n_{298}$ ($10^{20}$ cm$^{-3}$) | Bandgap (eV) |
|---|---|---|---|---|
| as-grown | 2150 | 37.4 | 3.56 | 3.88 |
| annealed | 2890 | 38.9 | 4.69 | 3.95 |

σ: conductivity;
μ: carrier mobility;
n: carrier concentration.

Further comparative data between as-grown and annealed films are shown in Tables 6 and 7 below. Generally, a 20-40% increase in electrical conductivity was observed in the annealed films compared to their as-grown form.

TABLE 6

Room temperature charge transport and optical properties of a $ZnIn_{2.0}Sn_yO_z$ film before annealing.

| Composition | Conductivity (S/cm) | Mobility ($cm^2/Vs$) | Carrier Concentration ($10^{20}$ $cm^{-3}$) |
|---|---|---|---|
| $ZnIn_{2.0}Sn_{0.83}O_z$ | 1002 | 35.8 | 1.75 |
| $ZnIn_{2.0}Sn_{1.05}O_z$ | 1290 | 38.2 | 2.12 |
| $ZnIn_{2.0}Sn_{1.16}O_z$ | 1644 | 34.8 | 2.95 |
| $ZnIn_{2.0}Sn_{1.50}O_z$ | 2150 | 37.4 | 3.56 |
| $ZnIn_{2.0}Sn_{1.68}O_z$ | 1860 | 34.2 | 3.41 |
| $ZnIn_{2.0}Sn_{1.79}O_z$ | 1530 | 29.0 | 3.30 |

σ: conductivity;
μ: carrier mobility;
n: carrier concentration; 0.85 < y 1.79.

TABLE 7

Room temperature charge transport and optical properties of a $ZnIn_{2.0}Sn_yO_z$ film after annealing.

| Composition | Conductivity (S/cm) | Mobility ($cm^2/Vs$) | Carrier Concentration ($10^{20}$ $cm^{-3}$) |
|---|---|---|---|
| $ZnIn_{2.0}Sn_{0.85}O_z$ | 1460 | 35.1 | 2.61 |
| $ZnIn_{2.0}Sn_{1.05}O_z$ | 1720 | 37.2 | 2.89 |
| $ZnIn_{2.0}Sn_{1.16}O_z$ | 2075 | 34.6 | 3.75 |
| $ZnIn_{2.0}Sn_{1.50}O_z$ | 2890 | 38.9 | 4.69 |
| $ZnIn_{2.0}Sn_{1.68}O_z$ | 2140 | 33.8 | 3.96 |
| $ZnIn_{2.0}Sn_{1.79}O_z$ | 1600 | 28.5 | 3.50 |

σ: conductivity;
μ: carrier mobility;
n: carrier concentration; 0.85 < y 1.79.

Example 17

Figure 15A:
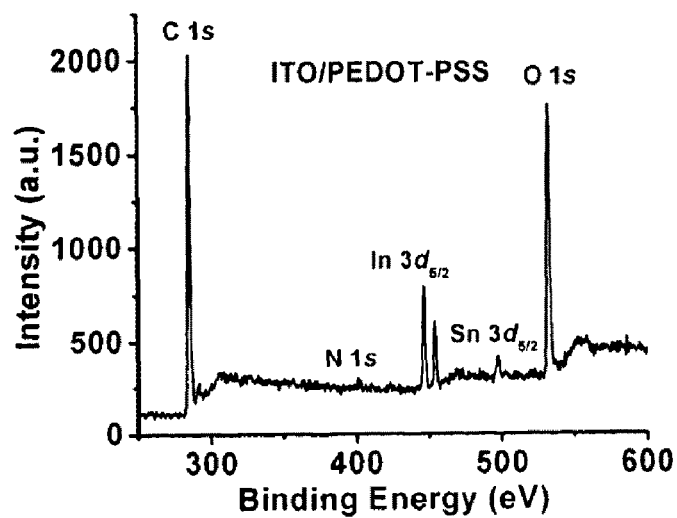
FIG. 15 is a comparison of the XPS spectra of an ITO/PEDOT-PSS sample (FIG. 14A) and a ZITO/PEDOT-PSS sample (FIG. 14B). Note that after heating in a vacuum oven at 200° C. for 1 hour, the ZITO/PEDOT-PSS sample has significantly less In contamination than does the ITO/PEDOT-PSS sample.
Figure 15B:
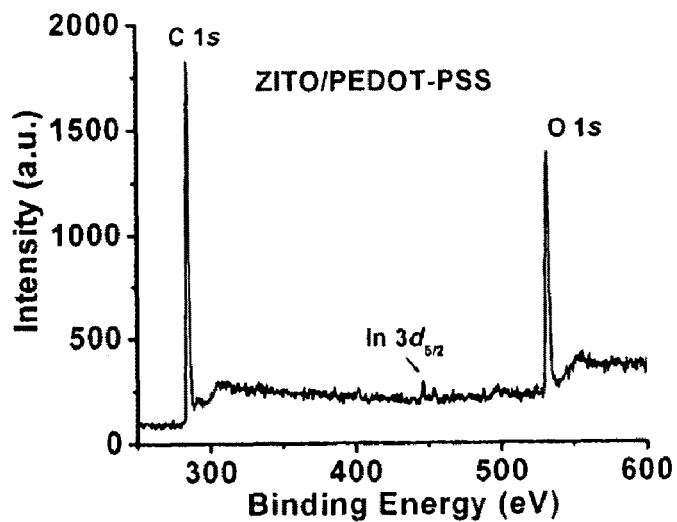

Polymer Light-Emitting Diode (PLED) Fabrication.
A. Synthesis of poly(9,9-dioctylfluorene), PFO.
Poly(9,9-dioctylfluorene) was synthesized following the procedures described in Yan et al. (2003), *Adv. Mater.*, 15: 835 and Lim et al. (2003), *Macromolecules*, 36: 4288. The chemical structure of PFO is shown in FIG. 15.
$M_n$: 54,700, $M_w$: 107,000, by GPC versus polystyrene standards. $^1$H NMR (CDCl$_3$, δ): 0.81 (t, 6H), 1.13-1.25 (m, 24H), 2.10-2.17 (m, 4H), 7.84 (d, 2H), 7.68 (m, 4H).

Figure 16:
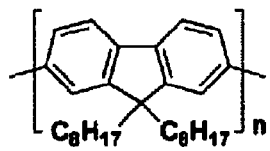
FIG. 16 shows the chemical structure of PFO, a typical component found in a polymer light emitting (PLED) device.

B. Fabrication of PLEDs
ZITO films with the nominal composition of $ZnIn_{2.0}Sn_{1.5}O_z$ were used in fabrication of polymer light-emitting diodes (PLEDs). Specifically, $ZnIn_{2.0}Sn_{1.5}O_z$-based and ITO-based PLED devices having conventional PLED structures (FIG. 16) were fabricated under identical conditions and at the same time. Surface cleaning and oxygen plasma treatment of both ZITO and ITO ensures that surface contamination is minimal. Thus, it is believed that the differences in PLED response were due to intrinsic differences in the anode materials.

Figure 17:
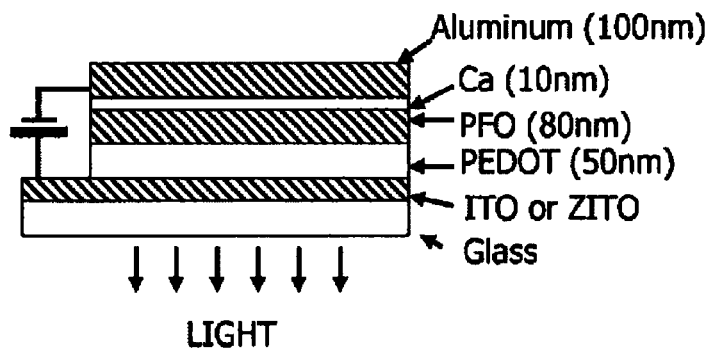
FIG. 17 shows the structure of a convention PLED.

As-grown $ZnIn_{2.0}Sn_{1.5}O_z$ and commercial ITO substrates (purchased from Colorado Concept, LLC) were first washed using a standard organic solvent/sonication procedure and then cleaned by a standard oxygen plasma treatment to remove surface contaminants. This was immediately followed by spincoating of a PEDOT-PSS solution (purchased from H. C. Starck). FIG. 17 shows the chemical structure of PEDOT-PSS.

The resulting films (thickness: ~50 nm) were dried in a vacuum oven at 150-200° C. for 1 hour, and then stored in an inert atmosphere glove box before an approximately 80 nm thick PFO layer was spincast on them from a xylene solution. The resulting samples were then dried in a vacuum oven overnight. Inside an inert atmosphere glove box, calcium (Ca) was thermally evaporated on top of PFO layer in a vacuum less than about $10^{-6}$ Torr, using a shadow mask to define the electrode area as 10 mm$^2$. Finally, an Al protective layer was thermally deposited on top of the Ca layer. The PLEDs were characterized under inert atmosphere inside a sealed aluminum sample container within 0.5 hr. after fabrication using instrumentation described elsewhere.

C. Response Characteristics of ZITO-Based Blue PLEDs
As-grown ZITO films with the nominal composition of $ZnIn_{2.0}Sn_{1.5}O_z$ were used as anodes in the fabrication of PLEDs due to their high conductivity. A control device with commercial ITO as the anode was also fabricated and evaluated at same time under identical conditions. The emissive material in the devices is poly(9,9-dioctylfluorene), a blue light-emitting polymer. The response characteristics of this device and of the control device based on commercial ITO are presented in FIG. 18. Both devices turn on at about 4 V, however the light output and current efficiency of the ZITO-based devices were as much as 70% greater than those of the ITO-based devices, while the current metrics of the two devices were comparable. At 9 V, the light output of the ZITO-based devices reached a maximum of about 4500 cd/m$^2$, greater than that of the ITO-based control devices and those of ITO-based blue light-emitting PLED devices reported in the literature employing PFO/PFO derivatives as the emissive layer.

The conductivity of the commercial ITO films used in control devices was measured to be 4400 S/cm, about twice that of the $ZnIn_2Sn_{1.5}O_z$ film. The sheet resistance of ITO was 18Ω/□, corresponding to a thickness of 130 nm. The sheet resistance and thickness of $ZnIn_2Sn_{1.5}O_z$ films were 24Ω/□ and 200 nm, respectively. Considering the small emissive area (~10 mm$^2$) of the devices, such sheet resistance should not lead to large voltage drop across TCO surface. Thus, it is believed that the thickness of anode material should not impact device response. Therefore, despite the fact that ITO is approximately twice as conductive as $ZnIn_{2.0}Sn_{1.5}O_z$, the difference in conductivity alone is not expected to affect device response such as turn-on voltage and current-voltage characteristics.

Figure 18:
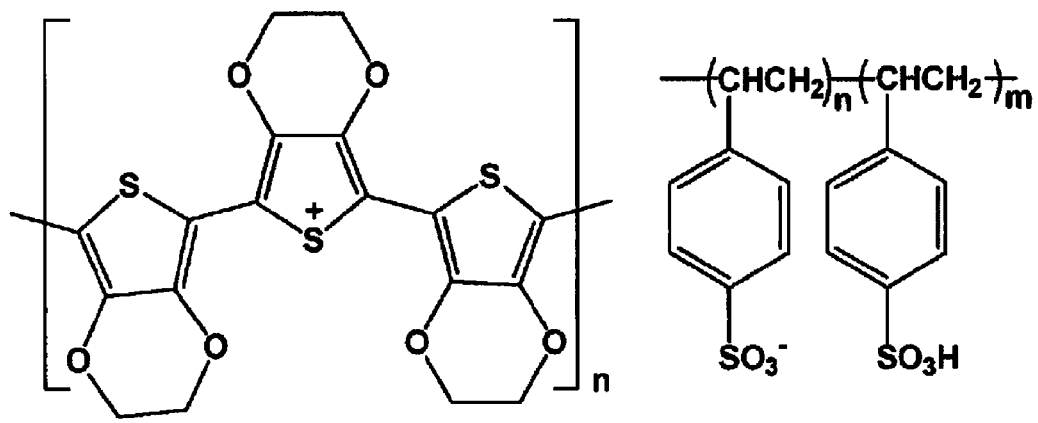
FIG. 18 shows the chemical structure of PEDOT-PSS, another typical component found in PLED.
Figure 19:
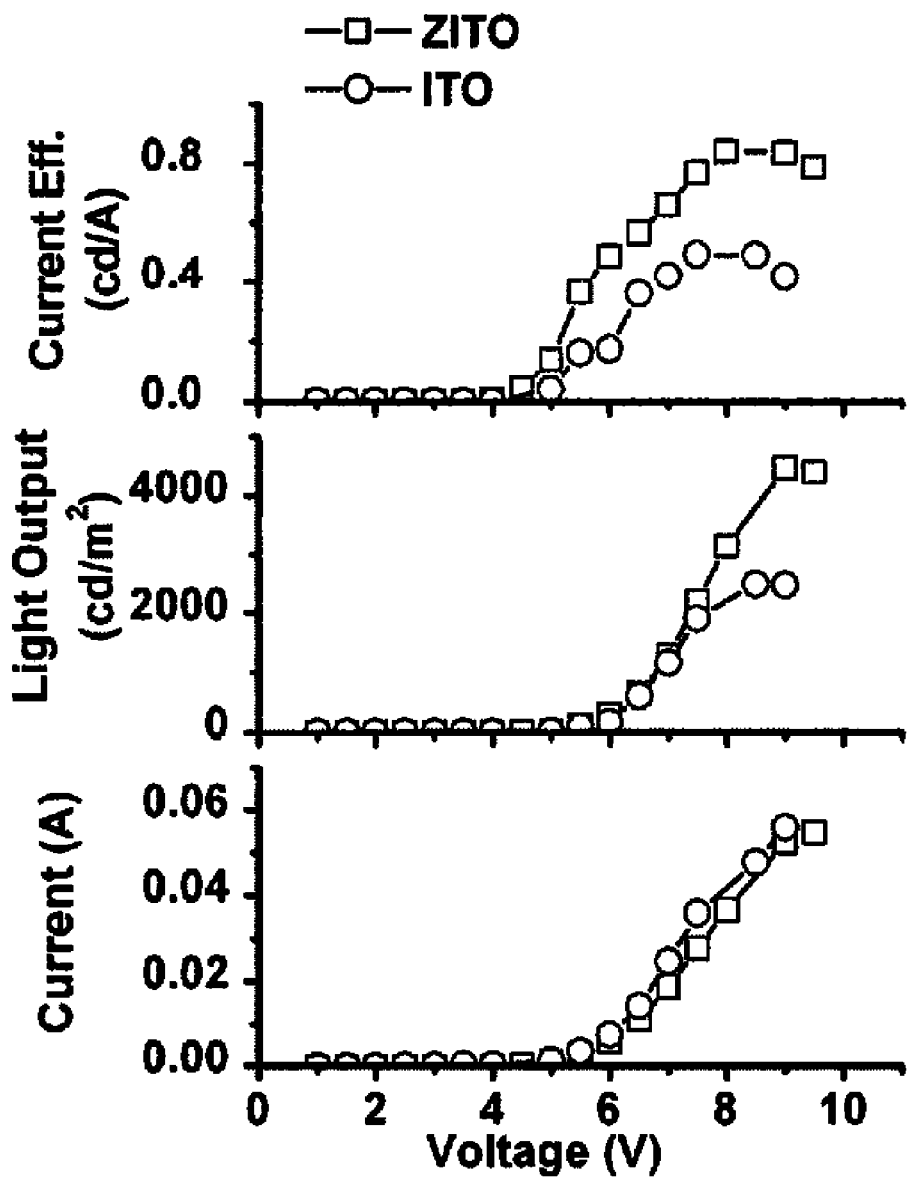
FIG. 19 shows the response of ITO-based vs. ZITO-based PLED devices have the structure shown in FIG. 17. Lines through data points are drawn as a guide to the eye.

Although the ZITO-based and ITO-based devices had similar current-voltage characteristics, the ZITO-based device had higher light output, hence higher current efficiency, than the ITO-based control device (FIG. 18). The difference may be attributed principally to the chemical resistance of ZITO towards PEDOT-PSS, and to a lesser degree, ZITO vs. ITO work function effects. The etching of ITO by PEDOT-PSS and the subsequent In diffusion into organic layers has been identified as one of the factors contributing to device degradation and reduced performance in both PLEDs and small molecule organic light-emitting diodes (OLEDs). The fact that MOCVD-derived ZITO thin films are about ten times less reactive with respect to PEDOT-PSS corrosion than commercial ITO films makes $ZnIn_{2.0}Sn_{1.5}O_z$/PEDOT-PSS interface more stable than the ITO/PEDOT-PSS interface. The increased interfacial stability suppresses the diffusion of In, which can serve as an exciton quenching center in the polymer emissive layer, and should subsequently enhance device response. Also since PFO-based PLED devices are hole-injection limited, better interfacial anode-organic contact over the electrode surface area should enhance efficiency-dependent hole injection.

Considering the reported high work function of $ZnIn_{2.0}Sn_{1.5}O_z$ films (5.2-5.4 eV versus about 4.5 eV for ITO) and its corresponding better energy alignment with PFO (HOMO: 5.9 eV), the hole transporting PEDOT-PSS layer might at first seem redundant. However, given the highly hydrophilic surface of the $ZnIn_{2.0}Sn_{1.5}O_z$ films, with an advancing aqueous contact angle of 23° (similar to that of ITO), the PEDOT-PSS may also function in the device as an adhesion layer to increase contact between the anode and the highly hydrophobic PFO. Furthermore, it has been argued that due to the near-metallic electronic structure of PEDOT-PSS, the work function of PEDOT-PSS (about 5.0 eV) should be essentially insensitive to the degenerately-doped oxide substrate work function. If this assessment is valid, then in devices that use PEDOT-PSS as the hole injection layer, the anode material work function should have minimal effects on device response arising from intrinsic injection barriers. This theory may explain why the expected effects of improved hole injection by using a high work function anode material, such as lowering of turn-on voltage for $ZnIn_{2.0}Sn_{1.5}O_z$-based device and attendant increase in current, are not immediately evident in this particular case.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:

1. A compound of a formula:

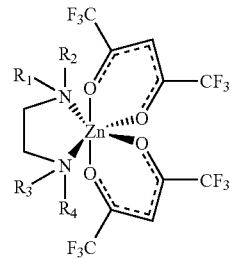

wherein $R_1$, $R_2$, $R_3$, and $R_4$ are selected from H and a methyl group, providing either $R_1$ and $R_2$ or $R_3$ and $R_4$ are methyl, or one of $R_1$ and $R_2$ is methyl and one of $R_3$ and $R_4$ is methyl, and at least one of $R_1$-$R_4$ is H.

* * * * *

UNITED STATES PATENT AND TRADEMARK OFFICE
CERTIFICATE OF CORRECTION

| | | |
|---|---|---|
| PATENT NO. | : 8,138,364 B2 | Page 1 of 1 |
| APPLICATION NO. | : 11/726624 | |
| DATED | : March 20, 2012 | |
| INVENTOR(S) | : Tobin J. Marks et al. | |

It is certified that error appears in the above-identified patent and that said Letters Patent is hereby corrected as shown below:

Column 1, Lines 12-16:

"The United States government has certain rights to this invention pursuant to Grant Nos. CHE-0201767 and DMR-0076097 from the United States National Science Foundation and Grant No. N00014-95-1-1-1319 from the Office of Naval Research, all to Northwestern University."
should be -- This invention was made with government support under grant numbers CHE 0201767 and DMR-0076097 awarded by the National Science Foundation and grant number N00014-95-1-1319 awarded by the Office of Naval Research. The government has certain rights in the invention. --

Signed and Sealed this
Fourteenth Day of August, 2012

David J. Kappos
*Director of the United States Patent and Trademark Office*